(12) United States Patent
Frick et al.

(10) Patent No.: US 7,288,528 B2
(45) Date of Patent: Oct. 30, 2007

(54) AROMATIC FLUOROGLYCOSIDE DERIVATIVES, MEDICAMENTS CONTAINING THESE COMPOUNDS, AND THE USE THEREOF

(75) Inventors: Wendelin Frick, Hunstetten-Beuerbach (DE); Heiner Glombik, Hofheim (DE); Werner Kramer, Mainz-Laubenheim (DE); Hubert Heuer, Schwabenheim (DE); Harm Brummerhop, Frankfurt (DE); Oliver Plettenburg, Hattersheim (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 270 days.

(21) Appl. No.: 10/735,179

(22) Filed: Dec. 12, 2003

(65) Prior Publication Data

US 2005/0014704 A1  Jan. 20, 2005

Related U.S. Application Data

(60) Provisional application No. 60/466,329, filed on Apr. 29, 2003.

(30) Foreign Application Priority Data

Dec. 12, 2002  (DE) .............................. 102 58 007

(51) Int. Cl.
C07H 17/02 (2006.01)
A61K 31/70 (2006.01)

(52) U.S. Cl. .................. 514/25; 514/42; 536/17.4; 536/18.4

(58) Field of Classification Search ............... 536/18.4, 536/1.11, 17.4; 514/25, 42
See application file for complete search history.

(56) References Cited

U.S. PATENT DOCUMENTS

| | | | |
|---|---|---|---|
| 5,190,923 A | 3/1993 | Vincent et al. | |
| 6,221,633 B1 | 4/2001 | Ertl et al. | |
| 6,221,897 B1 | 4/2001 | Frick et al. | |
| 6,245,744 B1 | 6/2001 | Frick et al. | |
| 6,342,512 B1 | 1/2002 | Kirsch et al. | |
| 6,515,117 B2* | 2/2003 | Ellsworth et al. | 536/17.2 |
| 6,624,185 B2 | 9/2003 | Glombik et al. | |
| 6,884,812 B2 | 4/2005 | Glombik et al. | |
| 2002/0132807 A1 | 9/2002 | Wang et al. | |
| 2002/0137903 A1 | 9/2002 | Ellsworth et al. | |

FOREIGN PATENT DOCUMENTS

| | | |
|---|---|---|
| EP | 0850948 | 7/1998 |
| EP | 0953357 | 11/1999 |
| EP | 1213296 A1 | 6/2002 |
| JP | 2000-80041 | 3/2000 |
| WO | WO95/23780 | 9/1995 |
| WO | WO97/26265 | 7/1997 |
| WO | WO97/41097 | 11/1997 |
| WO | WO97/49736 | 12/1997 |
| WO | WO98/08871 | 3/1998 |
| WO | WO99/03861 | 1/1999 |
| WO | WO99/15525 | 4/1999 |
| WO | WO 00/40569 | 7/2000 |
| WO | WO 00/63208 | 10/2000 |
| WO | WO 00/64876 | 11/2000 |
| WO | WO 00/64888 | 11/2000 |
| WO | WO 00/66585 | 11/2000 |
| WO | WO 00/71549 | 11/2000 |
| WO | WO 00/78312 | 12/2000 |
| WO | WO 01/09111 | 2/2001 |
| WO | WO 01/16147 | 3/2001 |
| WO | WO 01/27128 | 4/2001 |
| WO | WO 01/68660 | 9/2001 |
| WO | WO 01/74834 | 10/2001 |
| WO | WO 01/74835 | 10/2001 |
| WO | WO 01/83451 | 11/2001 |
| WO | WO 01/85695 | 11/2001 |
| WO | WO 01/91752 | 12/2001 |
| WO | WO 02/28872 | 4/2002 |

(Continued)

OTHER PUBLICATIONS

Diez-Sampedro, A., et. al., Residue 457 Controls Sugar Binding and Transport in the Na+/Glucose Cotransporter, The Journal of Biological Chemistry vol. 276, No. 52, Issue of Dec. 28, pp. 49188-49194, (2001).

(Continued)

*Primary Examiner*—Zinna N. Davis
(74) *Attorney, Agent, or Firm*—Barbara E. Kurys

(57) ABSTRACT

Novel aromatic fluoroglycoside derivatives, medicaments containing these compounds, and the use thereof.

The invention relates to substituted aromatic fluoroglycoside derivatives of the formula I

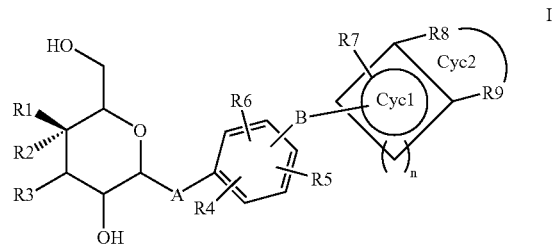

in which the radicals have the stated meanings, and their physiologically tolerated salts and process for their preparation. The compounds are suitable for example as antidiabetics.

13 Claims, No Drawings

FOREIGN PATENT DOCUMENTS

| | | |
|---|---|---|
| WO | WO 02/36602 | 5/2002 |
| WO | WO 02/44192 | 6/2002 |
| WO | WO 02/068439 | 9/2002 |
| WO | WO 02/068440 | 9/2002 |
| WO | WO 02/080935 | 10/2002 |
| WO | WO 02/080936 | 10/2002 |

OTHER PUBLICATIONS

Asakawa A., et. al., Cocaine-Amphetamine-Regulated Transcript Influences Energy Metabolism, Anxiety and Gastric Emptying in Mice, Hormone Metabolism Research, (2001), vol. 33, pp. 554-558.

Okada, H., et. al., Synthesis and Antitumor Activities of Prodrugs of Benzoylphenylureas, Chem. Pharm. Bull. vol. 42, Issue 1, 1994, pp. 57-61.

Lee D. W., et. al., Leptin agonists as a potential approach to the treatment of obesity, Drugs of the Future, (2001), vol. 26, No. 9, pp. 873-881.

Salvador, J., et. al., Perspectives In The Therapeutic Use Of Leptin, Expert Opinion Pharmacotherapy, (2001), vol. 2, No. 10, pp. 1615-1622.

Tyle, P. et. al., Iontophoretic Devices for Drug Delivery, Pharmaceutical Research, (1986), vol. 3, No. 6, pp. 318-326.

Withers, S.G., et. al. , 2-Deoxy-2-Fluoroglucosides: A Novel Class of Mechanism-Based Glucosidase Inhibitors, J. Am. Chem. Soc. (1987) vol. 109 pp. 7530-7531.

Zunfit, H. J. F., et. al., Carob Pulp Preparation for Treatment of Hypercholesterolemia, Advances In Therapy, (2001), vol. 18, No. 5, pp. 230-236.

\* cited by examiner

AROMATIC FLUOROGLYCOSIDE DERIVATIVES, MEDICAMENTS CONTAINING THESE COMPOUNDS, AND THE USE THEREOF

This application claims benefit of application Ser. No. 60/466,329 filed Apr. 29, 2003.

The invention relates to substituted aromatic fluoroglycoside derivatives, their physiologically tolerated salts and physiologically functional derivatives.

Several classes of substances having an SGLT effect have already been disclosed in the literature. The model for all these structures was the natural product phlorizin. From this were derived the following classes which are described in the property rights below:

propiophenone glycosides of Tanabe (WO 0280936, WO 0280935, JP 2000080041 and EP 850948)

2-(glucopyranoslyoxy)benzylbenzenes of Kissei (WO 0244192, WO 0228872 and WO 0168660)

glucopyranosyloxypyrazoles of Kissei and Ajinomoto (WO 0268440, WO 0268439, WO 0236602 and WO 0116147)

O-glycoside benzamides of Bristol-Myers Squibb (WO 0174835 and WO 0174834)

and C-aryl glycosides of Bristol-Myers Squibb (WO 0127128 and US 2002137903).

All the known structures contain glucose as a very important structural element.

Furthermore, diaryl sulfide compounds for the treatment of inflammatory and immune diseases are known from US 2002/132807. EP 0 953 357 A1 describes in general glycoside compounds as renal drug carriers and WO 95/23780 describes 4-hydroxyphenoxy-heterocycloalkyl compounds as skin lighteners.

The invention was based on the object of providing novel compounds with which it is possible to prevent and treat type 1 and type 2 diabetes. We have now surprisingly found that aromatic fluoroglycoside derivatives increase the effect on SGLT. These compounds are therefore particularly suitable for preventing and treating type 1 and type 2 diabetes.

The invention therefore relates to compounds of the formula I

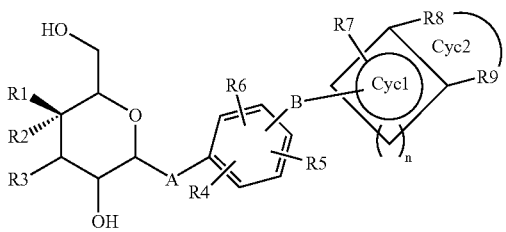

I wherein:
R1, R2 are each independently OH, F or H with the proviso that
  when R1 is F, R2 cannot be OH;
  when R1 is OH, R2 cannot be F; and
  when R1 is OH, R2 cannot be OH;
R3 is OH or F with the proviso that at least one of said R1, R2, R3 radicals must be F;
A is O, NH, $CH_2$, S or a bond;
R4, R5, R6 are each independently hydrogen, F, Cl, Br, I, OH, $NO_2$, CN, COOH,
$CO(C_1-C_6)$-alkyl, $COO(C_1-C_6)$-alkyl, $CONH_2$, $CONH(C_1-C_6)$-alkyl, $CON[(C_1-C_6)$-alkyl$]_2$, $(C_1-C_6)$-alkyl, $(C_2-C_6)$-alkenyl, $(C_2-C_6)$-alkynyl, $(C_1-C_6)$-alkoxy, $HO(C_1-C_6)$-alkyl, $(C_1-C_6)$-alkyl-O—$(C_1-C_6)$-alkyl, phenyl or benzyl,
  wherein said $CO(C_1-C_6)$-alkyl, $COO(C_1-C_6)$-alkyl, $CONH(C_1-C_6)$-alkyl, $CON[(C_1-C_6)$-alkyl$]_2$, $(C_1-C_6)$-alkyl, $(C_2-C_6)$-alkenyl, $(C_2-C_6)$-alkynyl, $(C_1-C_6)$-alkoxy, $HO(C_1-C_6)$-alkyl, $(C_1-C_6)$-alkyl-O—$(C_1-C_6)$-alkyl radicals are optionally substituted with one or more fluorine atoms,
$SO_2$—$NH_2$, $SO_2NH(C_1-C_6)$-alkyl, $SO_2N[(C_1-C_6)$-alkyl$]_2$, S—$(C_1-C_6)$-alkyl, S—$(CH_2)_o$-phenyl, SO—$(C_1-C_6)$-alkyl, SO—$(CH_2)_o$-phenyl, $SO_2$—$(C_1-C_6)$-alkyl, $SO_2$—$(CH_2)_o$-phenyl,
  wherein the phenyl ring of said S—$(CH_2)_o$-phenyl, SO—$(CH_2)_o$-phenyl and $SO_2$—$(CH_2)_o$-phenyl radicals may be mono- or disubstituted with F, Cl, Br, OH, $CF_3$, $NO_2$, CN, $OCF_3$, O—$(C_1-C_6)$-alkyl, $(C_1-C_6)$-alkyl or $NH_2$ and wherein o is 0, 1, 2, 3, 4, 5 or 6,
$NH_2$, NH—$(C_1-C_6)$-alkyl, $N((C_1-C_6)$-alkyl$)_2$, $NH(C_1-C_7)$-acyl, phenyl, O—$(CH_2)_o$-phenyl,
  wherein the phenyl ring of said phenyl and O—$(CH_2)_o$-phenyl radicals may be mono-, di-, or trisubstituted with F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, COOH, COO—$(C_1-C_6)$-alkyl or $CONH_2$ and wherein o is as hereinabove defined;
B is $(C_0-C_{15})$-alkanediyl,
  wherein one or more carbon atoms in said $(C_0-C_{15})$-alkanediyl radical are, independently of one another, optionally replaced by —O—, —(C=O)—, —CH=CH—, —C≡C—, —S—, —CH(OH)—, —CHF—, —$CF_2$—, —(S=O)—, —($SO_2$)—, —N(($C_1-C_6$)-alkyl)-, —N(($C_1-C_6$)-alkyl-phenyl)- or —NH—;
n is 0, 1, 2, 3 or 4;
Cyc1 is a 3-, 4-, 5-, 6-, or 7-membered saturated, partially saturated or unsaturated ring, wherein one carbon atom of said ring may be replaced by O, N or S;
R7, R8, R9 R7, R8, and R9 are each independently hydrogen, F, Cl, Br, I, OH, $CF_3$,
  $NO_2$, CN, COOH, $COO(C_1-C_6)$-alkyl, $CO(C_1-C_4)$-alkyl, $CONH_2$, $CONH(C_1-C_6)$-alkyl, $CON[(C_1-C_6)$-alkyl]2, $(C_1-C_6)$-alkyl, $(C_2-C_6)$—, alkenyl, $(C_2-C_6)$-alkynyl, $(C_1-C_8)$-alkoxy, HO—$(C_1-C_6)$-alkyl, $(C_1-C_6)$-alkyl-O—$(C_1-C_6)$-alkyl,
    wherein said $COO(C_1-C_6)$-alkyl, $CO(C_1-C_4)$-alkyl, $CONH(C_1-C_6)$-alkyl, $CON[(C_1-C_6)$-alkyl$]_2$, $(C_1-C_6)$-alkyl, $(C_2-C_6)$-alkenyl, $(C_2-C_6)$-alkynyl, $(C_1-C_8)$-alkoxy, HO—$(C_1-C_6)$-alkyl and $(C_1-C_6)$-alkyl-O—$(C_1-C_6)$-alkyl radicals are optionally substituted with one or more fluorine atoms,
  $SO_2$—$NH_2$, $SO_2NH(C_1-C_6)$-alkyl, $SO_2N[(C_1-C_6)$-alkyl$]_2$, S—$(C_1-C_6)$-alkyl, S—$(CH_2)_o$-phenyl, SO—$(C_1-C_6)$-alkyl, SO—$(CH_2)_o$-phenyl, $SO_2$—$(C_1-C_6)$-alkyl, $SO_2$—$(CH_2)_o$-phenyl,
    wherein said $SO_2NH(C_1-C_6)$-alkyl, $SO_2N[(C_1-C_6)$-alkyl$]_2$, S—$(C_1-C_6)$-alkyl, SO—$(C_1-C_6)$-alkyl and $SO_2$—$(C_1-C_6)$-alkyl radicals are optionally substituted with one or more fluorine atoms, and wherein the phenyl ring of said S—$(CH_2)_o$-phenyl, SO—$(CH_2)_o$-phenyl and $SO_2$—$(CH_2)_o$-phenyl radicals is optionally mono- or disubstituted with F, Cl, Br, OH, CF$_3$, NO$_2$, CN, OCF3, O—(C$_1$-C$_6$)-alkyl, (C$_1$-C$_6$)-alkyl or NH$_2$, and wherein o is as hereinabove defined, NH$_2$, NH—(C$_1$-C$_6$)-alkyl, N((C$_1$-C$_6$)-alkyl)$_2$, NH(C$_1$-C$_7$)-acyl, phenyl or O—(CH$_2$)$_o$-phenyl, wherein the phenyl ring of said phenyl and O—(CH$_2$)$_o$-phenyl radicals is optionally mono-, di-, or trisubstituted with F, Cl, Br, I, OH, CF$_3$, NO$_2$, CN, OCF$_3$, (C$_1$-C$_8$)-alkoxy, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl or CONH$_2$, and wherein o is as hereinabove defined;

or R8 and R9 taken together with the carbon atoms to which they are attached form a 5-, 6- or 7-membered, saturated, partially saturated or unsaturated ring herein referred to as Cyc2, wherein one or two carbon atom(s) in said Cyc2 ring is optionally replaced by N, O or S, and wherein said Cyc2 ring is optionally substituted with (C$_1$-C$_6$)-alkyl, (C$_2$-C$_5$)-alkenyl or (C$_2$-C$_5$)-alkynyl, wherein said (C$_1$-C$_6$)-alkyl, (C$_2$-C$_5$)-alkenyl and (C$_2$-C$_5$)-alkynyl radicals are optionally substituted with F, Cl, OH, CF$_3$, NO$_2$, CN, COO(C$_1$-C$_4$)-alkyl, CONH$_2$, CONH(C$_1$-C$_4$)-alkyl or OCF$_3$, and wherein a —CH$_2$— group contained in said (C$_1$-C$_6$)-alkyl, (C$_2$-C$_5$)-alkenyl and (C$_2$-C$_5$)-alkynyl radicals is optionally replaced by —O—;

and pharmaceutically acceptable salts thereof.

The linkage points of R4, R5, R6 and B to the phenyl ring can be freely selected. All resulting compounds of the formula I belong to the present invention. Compounds of the formula I in which the B substituent on the phenyl ring is disposed in the position ortho (neighboring position) to the A substituent are preferred.

Preferred compounds of the formula I are those wherein:

R1 and R2 are each independently OH, F or H with the proviso that at least one of said radicals R1 and R2 must be F and with the further proviso that when R1 is F, R2 is not OH, when R1 is OH, R2 is not F, and when R1 is OH, R2 is not OH;

R3 is OH;

A is O or NH;

R4, R5, R6 are each independently hydrogen, F, Cl, Br, I, OH, NO$_2$, CN, COOH,

CO(C$_1$-C$_6$)-alkyl, COO(C$_1$-C$_6$)-alkyl, CONH$_2$, CONH(C$_1$-C$_6$)-alkyl, CON [(C$_1$-C$_6$)-alkyl]$_2$, (C$_1$-C$_6$)-alkyl, (C$_2$-C$_6$)-alkenyl, (C$_2$-C$_6$)-alkynyl, (C$_1$-C$_6$)-alkoxy, HO(C$_1$-C$_6$)-alkyl, (C$_1$-C$_6$)-alkyl-O—(C$_1$-C$_6$)-alkyl, phenyl, benzyl or SO—(C$_1$-C$_6$)-alkyl, wherein said CO(C$_1$-C$_6$)-alkyl, COO(C$_1$-C$_6$)-alkyl, CONH(C$_1$-C$_6$)-alkyl, CON[(C$_1$-C$_6$)-alkyl]$_2$, (C$_1$-C$_6$)-alkyl, (C$_2$-C$_6$)-alkenyl, (C$_2$-C$_6$)-alkynyl, (C$_1$-C$_6$)-alkoxy, HO(C$_1$-C$_6$)-alkyl, (C$_1$-C$_6$)-alkyl-O—(C$_1$-C$_6$)-alkyl and SO—(C$_1$-C$_6$)-alkyl radicals are optionally substituted with one or more fluorine atoms, B is (C$_0$-C$_{15}$)-alkanediyl, wherein one or more of the carbon atoms in said alkanediyl radical may be replaced, independently of one another, with —O—, —(C=O)—, —CH=CH—, —C≡C—, —S—, —CH(OH)—, —CHF—, —CF$_2$—, —(S=O)—, —(SO$_2$)—, —N((C$_1$-C$_6$)-alkyl)-, —N((C$_1$-C$_6$)-alkyl-phenyl)- or —NH—;

n is 0, 1, 2, 3 or 4;

Cyc1 is a 3-, 4-, 5-, 6- or 7-membered saturated, partially saturated or unsaturated ring, wherein one carbon atom of said ring may be replaced by O, N or S;

R7, R8 and R9 are each independently hydrogen, F, Cl, Br, I, OH, CF$_3$, NO$_2$, CN, COOH, COO(C$_1$-C$_6$)-alkyl, CO(C$_1$-C$_4$)-alkyl, CONH$_2$, CONH(C$_1$-C$_6$)-alkyl, CON[(C$_1$-C$_6$)-alkyl]$_2$, (C$_1$-C$_6$)-alkyl, (C$_2$-C$_6$)-alkenyl, (C$_2$-C$_6$)-alkynyl, (C$_1$-C$_8$)-alkoxy, HO—(C$_1$-C$_6$)-alkyl, (C$_1$-C$_6$)-alkyl-O—(C$_1$-C$_6$)-alkyl and SO—(C$_1$-C$_6$)-alkyl, wherein said COO(C$_1$-C$_6$)-alkyl, CO(C$_1$-C$_4$)-alkyl, CONH(C$_1$-C$_6$)-alkyl, CON[(C$_1$-C$_6$)-alkyl]$_2$, (C$_1$-C$_6$)-alkyl, (C$_2$-C$_6$)-alkenyl, (C$_2$-C$_6$)-alkynyl, (C$_1$-C$_8$)-alkoxy, HO—(C$_1$-C$_6$)-alkyl, (C$_1$-C$_6$)-alkyl-O—(C$_1$-C$_6$)-alkyl and SO—(C$_1$-C$_6$)-alkyl radicals are optionally substituted with one or more fluorine atoms, or R8 and R9 taken together with the carbon atoms to which they are attached form a 5-, 6- or 7-membered, saturated, partially saturated or unsaturated ring herein referred to as Cyc2, wherein one or two carbon atom(s) in said Cyc2 ring are optionally replaced by N, O or S, and wherein said Cyc2 ring is optionally substituted with (C$_1$-C$_6$)-alkyl, (C$_2$-C$_5$)-alkenyl or (C$_2$-C$_5$)-alkynyl, wherein said (C$_1$-C$_6$)-alkyl, (C$_2$-C$_5$)-alkenyl and (C$_2$-C$_5$)-alkynyl radicals are optionally substituted with F, Cl, OH, CF$_3$, NO$_2$, CN, COO(C$_1$-C$_4$)-alkyl, CONH$_2$, CONH(C$_1$-C$_4$)-alkyl or OCF$_3$, and wherein a —CH$_2$— group contained in said (C$_1$-C$_6$)-alkyl, (C$_2$-C$_5$)-alkenyl and (C$_2$-C$_5$)-alkynyl radicals is optionally replaced by —O—.

Further preferred compounds of the formula I are those in which the sugar residues are beta(β)-linked and the stereochemistry in the 2, 3 and 5 position of the sugar residue has the D-gluco configuration.

Particularly preferred compounds of formula I are those wherein:

R1 and R2 are each independently OH, F or H with the proviso that at least one of said radicals R1 and R2 must be F and with the further proviso that when R1 is F, R2 is not OH, when R1 is OH, R2 is not F, and when R1 is OH, R2 is not OH, R3 is OH;

A is O;

R4, R5, R6 are each independently hydrogen, F, Cl, Br, I, OH, NO$_2$, CN, COOH,

CF3, OCF3, OCH2CF3, (C$_1$-C$_4$)alkyl-CF2—, COO(C$_1$-C$_6$)-alkyl, (C$_1$-C$_6$)-alkyl, (C$_2$-C$_6$)-alkenyl, (C$_2$-C$_6$)-alkynyl, (C$_1$-C$_6$)-alkoxy, HO(C$_1$-C$_6$)-alkyl, (C$_1$-C$_6$)-alkyl-O—(C$_1$-C$_6$)-alkyl, phenyl or benzyl, B is (C$_1$-C$_4$)-alkanediyl, wherein one or more of the carbon atoms in said alkanediyl radical may be replaced, independently of one another, with —O—, —(C=O)—, —CH(OH)—, —CH F—, —CF2—, —CO—N(C$_1$-C$_6$)-alkyl)-, —CO—NH— or —NH—;

n is 2 or 3;

Cyc1 is an unsaturated 5- or 6-membered ring, wherein one carbon atom of said ring may be replaced by O, N or S;

R7, R8, and R9 are each independently hydrogen, F, Cl, Br, OH, (C$_1$-C$_6$)-alkyl, (C$_1$-C$_8$)-alkoxy, HO—(C$_1$-C$_6$)-alkyl or (C$_1$-C$_6$)-alkyl-O—(C$_1$-C$_6$)-alkyl, or R8 and R9 taken together form the radicals —CH=CH—O—, —CH$_2$—CH$_2$-O—, —CH=CH—S—, —CH=CH—CH=CH—, —O—(CH$_2$)P—O— wherein p is 1 or 2 and with the carbon atoms to which said radicals are attached form a 5- or 6-membered, saturated, partially saturated or completely unsaturated ring and, in such instance, R7 is preferably methyl, ethyl, OMe, F, Cl, Br or H.

Very particularly preferred compounds of the formula I are those wherein:
R1 is F and R2 is H;
R1 is H and R2 is F; or
R1 is F and R2 is F
R3 is OH;
A is O;
R4, R5, R6 are each independently hydrogen, OH, $(C_1-C_4)$-alkoxy, $CF_3$, $(C_1-C_4)$-alkyl, F, Cl, Br or I
B is —$CH_2$—, —$C_2H_4$—, —$C_3H_6$—, —CH(OH)—, —(C=O)—, —CO—NH—$CH_2$—, —CO—$CH_2$—$CH_2$—, —O— or —NH—;
n is 2 or 3;
Cyc1 is an unsaturated 6-membered ring, wherein one carbon atom of said 6-membered ring may be replaced by N, or
an unsaturated 5-membered ring, wherein one carbon atom of said 5-membered ring may be replaced by S;
R7, R8, R9 are each independently hydrogen, OH, $(C_1-C_4)$-alkyl, $(C_1-C_7)$-alkoxy, $OCF_3$ or halogen or
R8 and R9 taken together form the radicals —CH=CH—O—, —$CH_2$—$CH_2$—O—, —CH=CH—CH=CH— or —O—$(CH_2)_p$—O— wherein p is 1 or 2, and, with the carbon atoms to which they are attached, form a 5- or 6-membered ring, and, in such instance, R7 is preferably methyl, ethyl, methoxy, F, Cl, Br or hydrogen.

Further very particularly preferred are compounds of the formula Ia

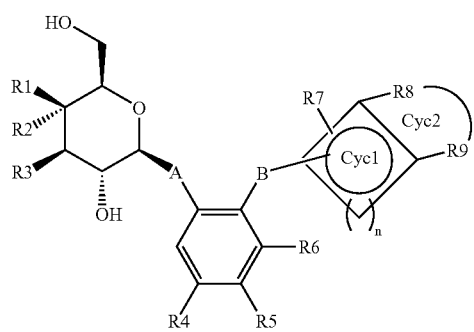

Ia wherein
R1 is F and R2 is H;
R1 is H and R2 is F; or
R1 is F and R2 is F;
R3 is OH;
A is O;
R4 is hydrogen, $(C_1-C_4)$-alkyl, $(C_1-C_4)$-alkoxy or OH;
R5 is hydrogen, F, methoxy or ethoxy;
R6 is hydrogen or OH;
B is —$CH_2$—, —CO—NH—$CH_2$—; —O— or —CO—$CH_2$—$CH_2$—;
Cyc1 is phenyl or thiophene;
R7, R8, R9 are hydrogen, OH, Cl, $OCF_3$, $(C_1-C_4)$-alkyl or $(C_1-C_4)$-alkoxy; or
R8 and R9 taken together form —CH=CH—O—, —CH=CH—CH=CH— or —$CH_2$—$CH_2$—O— and, with the carbon atoms to which they are attached, form a 5- or 6-membered ring, and, in such instance, R7 is preferably hydrogen.

Compounds of particularly preferred importance are also those of the formula Ib

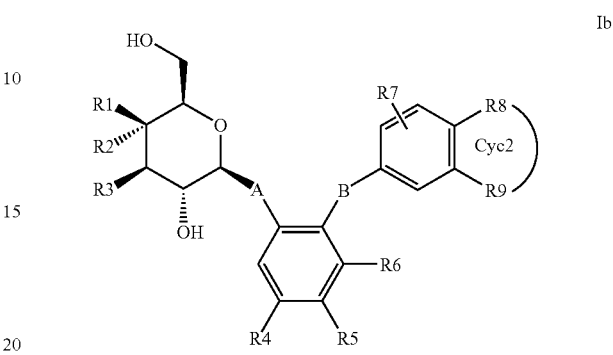

Ib wherein
R1 is F and R2 is H;
R1 is H and R2 is F; or
R1 is F and R2 is F;
R3 is OH;
A is O;
R4 is hydrogen, methyl, methoxy or OH;
R5 is hydrogen, F or methoxy;
R6 is hydrogen or OH;
B is —$CH_2$—, —CO—NH—$CH_2$—, —O— or —CO—$CH_2$—$CH_2$—;
Cyc1 is phenyl;
R7 is hydrogen;
R8 is hydrogen, OH, ethyl, Cl, $OCF_3$ or methoxy;
R9 is hydrogen; or
R8 and R9 taken together form —CH=CH—O— or —$CH_2$—$CH_2$—O—, and, with the carbon atoms to which they are attached form a 5-membered ring.

Additional very particularly preferred compounds of the formula I are those in which R1 is H and R2 is F.

The invention relates to compounds of the formula I in the form of their racemates, racemic mixtures and pure enantiomers and to their diastereomers and mixtures thereof.

The alkyl radicals in the substituents R4, R5, R6, R7, R8 and R9 may be either straight-chain or branched. Halogen means F, Cl, Br or I, preferably F or Cl.

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not. Carbonates at the 6 position of the sugar (see WO 0280936 and WO 0244192) are preferred, particularly preferably methyl carbonate and ethyl carbonate.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

The compound(s) of formula (I) may also be administered in combination with other active ingredients.

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg and 50 mg) per day and per kilogram of bodyweight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, tablets or capsules, may contain, for example, from 1.0 to 1000 mg, typically from 10 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The invention additionally relates to processes for preparing the compounds of the formula I, which can be obtained in accordance with the following reaction schemes of processes A to F.

Process A:

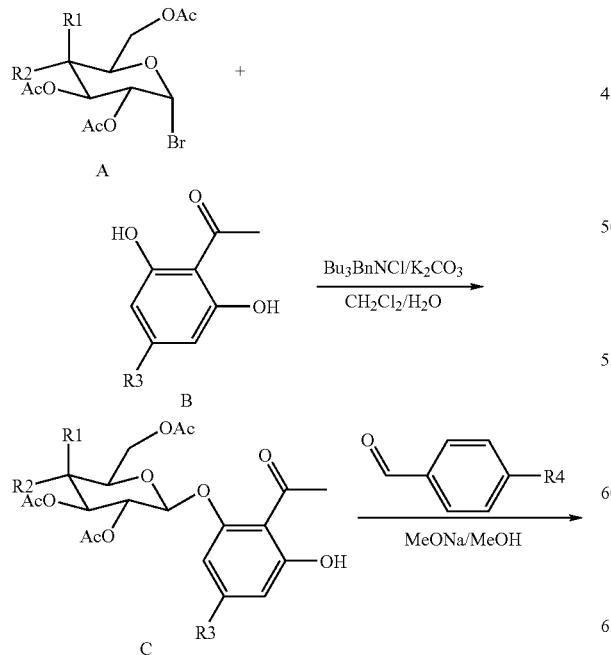

Process B:

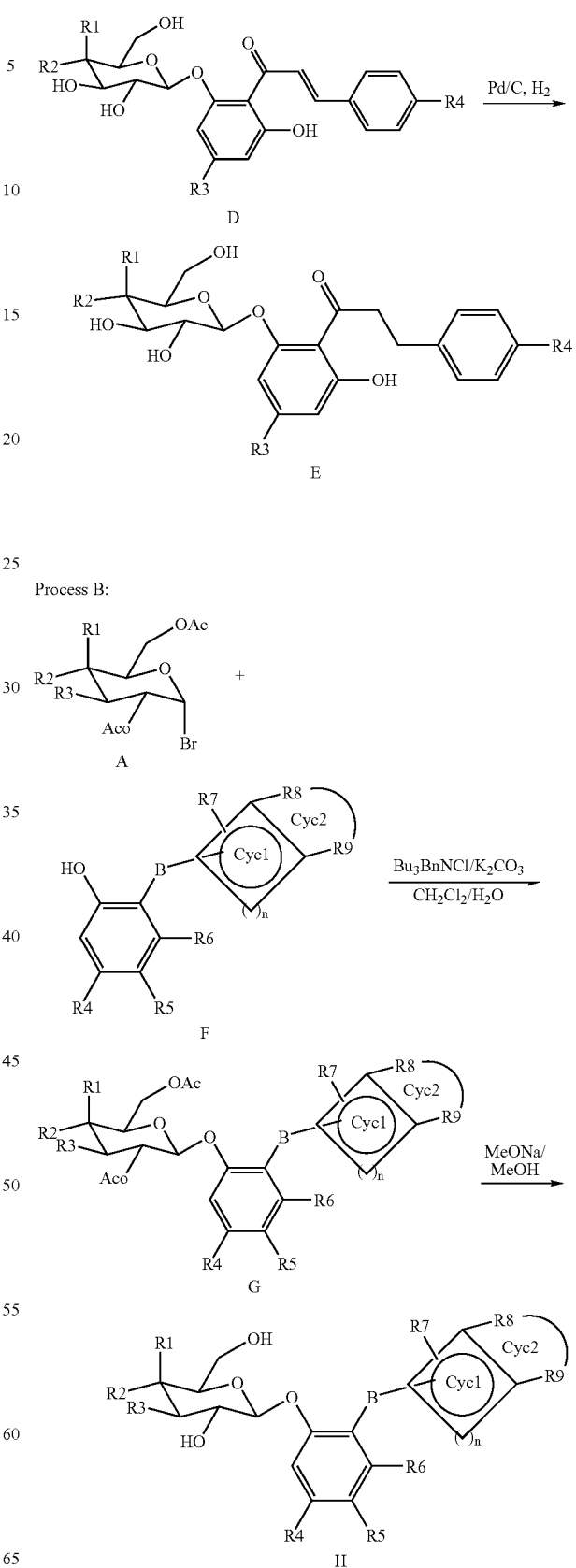

Process C:
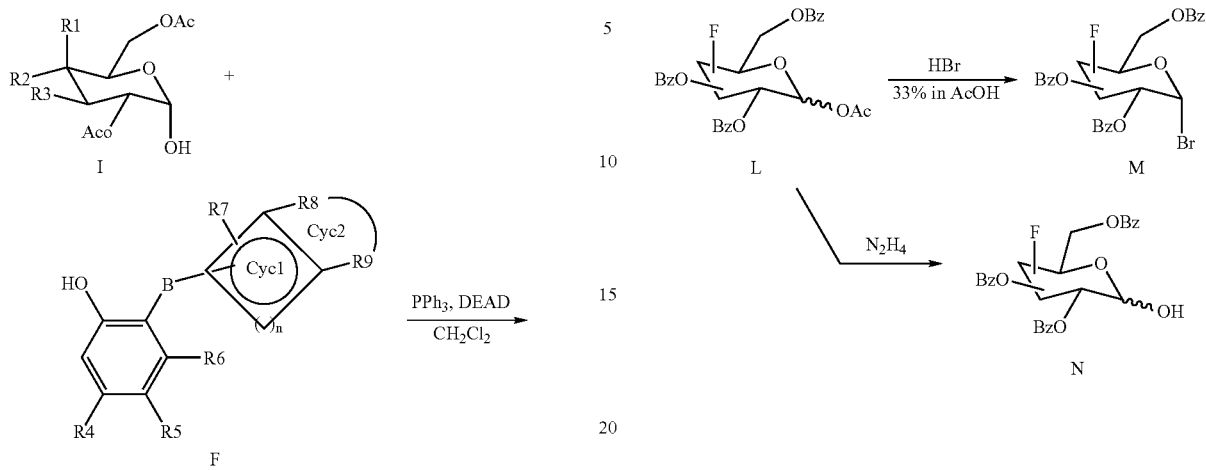
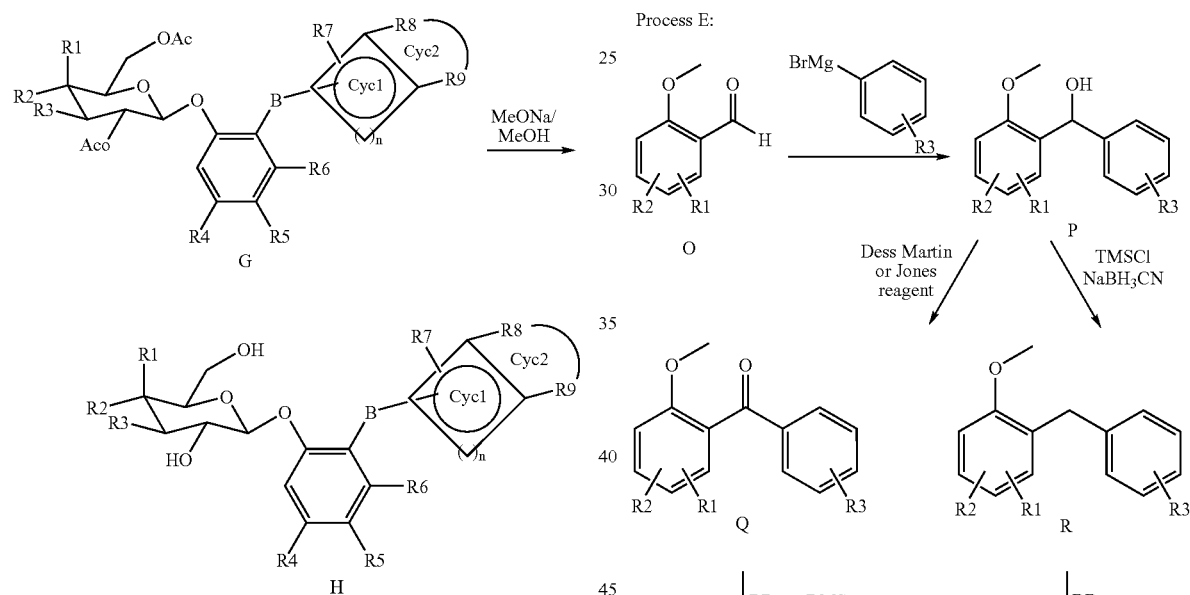
Process D:
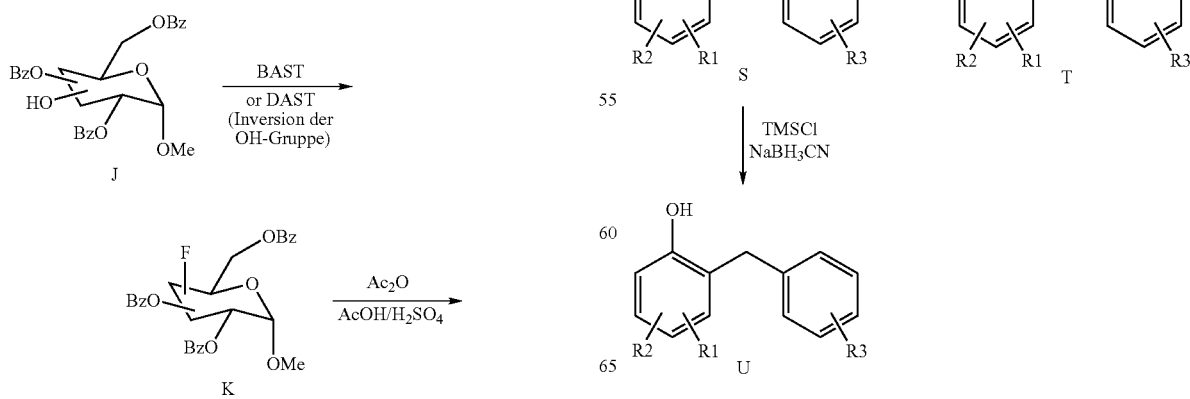

Process F:

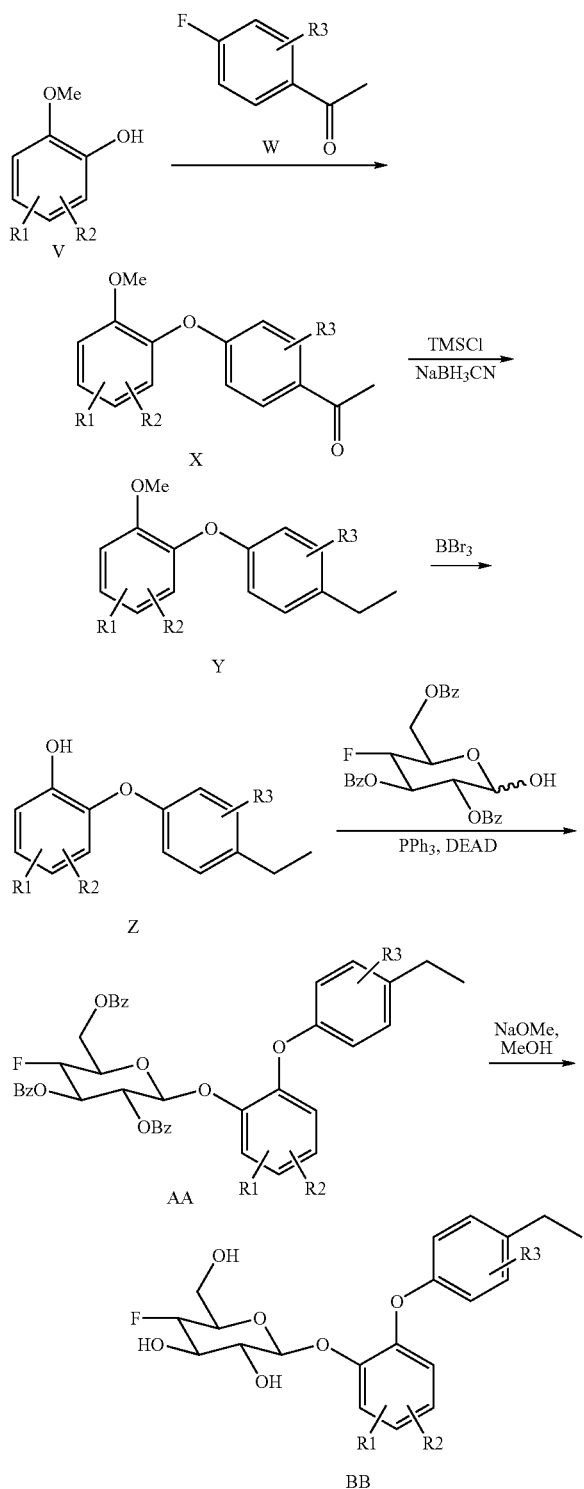

The schemes depicted for processes A-F are self-explanatory and can be carried out thus by the skilled worker. More details are, nevertheless, indicated in the experimental part. The compounds of examples 1 to 24 were obtained by processes A-F. Other compounds of the formula I can be obtained correspondingly or by known processes.

The compound(s) of the formula I can also be administered in combination with other active ingredients.

Further active ingredients suitable for combination products are: all antidiabetics mentioned in the Rote Liste 2001, chapter 12. They may be combined with the compounds of the formula I of the invention in particular for synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964, fast-acting insulins (see U.S. Pat. No. 6,221,633), GLP-1 derivatives such as, for example, those disclosed in WO 98/08871 of Novo Nordisk A/S, and orally effective hypoglycemic active ingredients.

The orally effective hypoglycemic active ingredients include, preferably, sulfonylureas, biguanides, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk A/S, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMGCoA reductase inhibitor such as simvastatin, fluvastatin, pravastatin, lovastatin, atorvastatin, cerivastatin, rosuvastatin.

In one embodiment of the invention, the compounds of the formula I are administered in combination with a cholesterol absorption inhibitor such as, for example, ezetimibe, tiqueside, pamaqueside.

In one embodiment of the invention, the compounds of the formula I are administered in combination with a PPAR gamma agonist, such as, for example, rosiglitazone, pioglitazone, JTT-501, GI 262570.

In one embodiment of the invention, the compounds of the formula I are administered in combination with a PPAR alpha agonist, such as, for example, GW 9578, GW 7647.

In one embodiment of the invention, the compounds of the formula I are administered in combination with a mixed PPAR alpha/gamma agonist, such as, for example, GW 1536, AVE 8042, AVE 8134, AVE 0847, AVE 0897 or as described in WO 00/64888, WO 00/64876, WO 03/20269.

In one embodiment of the invention, the compounds of the formula I are administered in combination with a fibrate such as, for example, fenofibrate, clofibrate, bezafibrate.

In one embodiment of the invention, the compounds of the formula I are administered in combination with an MTP inhibitor such as, for example, implitapide, BMS-201038, R-103757.

In one embodiment of the invention, the compounds of the formula I are administered in combination with bile acid absorption inhibitor (see, for example, U.S. Pat. No. 6,245,744 or U.S. Pat. No. 6,221,897), such as, for example, HMR 1741.

In one embodiment of the invention, the compounds of the formula I are administered in combination with a CETP inhibitor, such as, for example, JTT-705.

In one embodiment of the invention, the compounds of the formula I are administered in combination with a polymeric bile acid adsorbent such as, for example, cholestyramine, colesevelam.

In one embodiment of the invention, the compounds of the formula I are administered in combination with an LDL receptor inducer (see U.S. Pat. No. 6,342,512), such as, for example, HMR1171, HMR1586.

In one embodiment of the invention, the compounds of the formula I are administered in combination with an ACAT inhibitor, such as, for example, avasimibe.

In one embodiment of the invention, the compounds of the formula I are administered in combination with an antioxidant, such as, for example, OPC-14117.

In one embodiment of the invention, the compounds of the formula I are administered in combination with a lipoprotein lipase inhibitor, such as, for example, NO-1886.

In one embodiment of the invention, the compounds of the formula I are administered in combination with an ATP-citrate lyase inhibitor, such as, for example, SB-204990.

In one embodiment of the invention, the compounds of the formula I are administered in combination with a squalene synthetase inhibitor, such as, for example, BMS-188494.

In one embodiment of the invention, the compounds of the formula I are administered in combination with a lipoprotein(a) antagonist, such as, for example, CI-1027 or nicotinic acid.

In one embodiment of the invention, the compounds of the formula I are administered in combination with a lipase inhibitor, such as, for example, orlistat.

In one embodiment of the invention, the compounds of the formula I are administered in combination with insulin.

In one embodiment, the compounds of the formula I are administered in combination with a sulfonylurea such as, for example, tolbutamide, glibenclamide, glipizide or glimepiride.

In one embodiment, the compounds of the formula I are administered in combination with a biguanide, such as, for example, metformin.

In one further embodiment, the compounds of the formula I are administered in combination with a meglitinide, such as, for example, repaglinide.

In one embodiment, the compounds of the formula I are administered in combination with a thiazolidinedione, such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compounds of the formula I are administered in combination with an α-glucosidase inhibitor, such as, for example, miglitol or acarbose.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with more than one of the aforementioned compounds, e.g. in combination with a sulfonylurea and metformin, with a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A., et al., M.: Hormone and Metabolic Research (2001), 33(9), 554-558), NPY antagonists, e.g. naphthalene-1-sulfonic acid {4-[(4-aminoquinazolin-2-ylamino)methyl]-cyclohexylmethyl}amide; hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin-4-ylurea; hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl] dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tert-butyl ester (WO 01/85695)), TRH agonists (see, for example, EP 0 462 884) uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active ingredient is dexamphetamine or amphetamine.

In one embodiment, the other active ingredient is fenfluramine or dexfenfluramine.

In another embodiment, the other active ingredient is sibutramine.

In one embodiment, the other active ingredient is orlistat.

In one embodiment, the other active ingredient is mazindol or phentermine.

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 Sep-Oct), 18(5), 230-6.) Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is regarded as falling within the protection conferred by the present invention.

The citation of any reference herein should not be construed as an admission that such reference is available as "Prior Art" to the instant application.

Various publications are cited herein, the disclosures of which are incorporated by reference in their entireties.

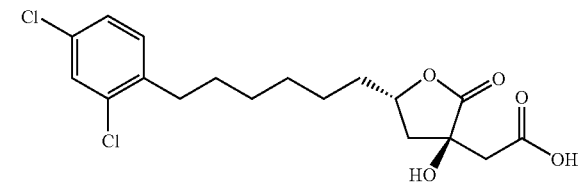

SB-204990

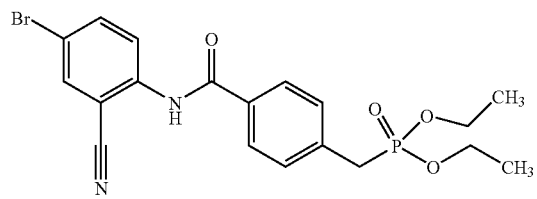

NO-1886

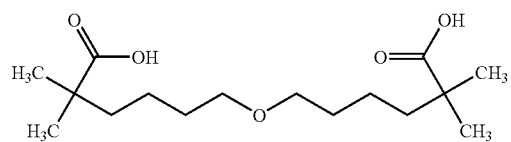

Cl-1027

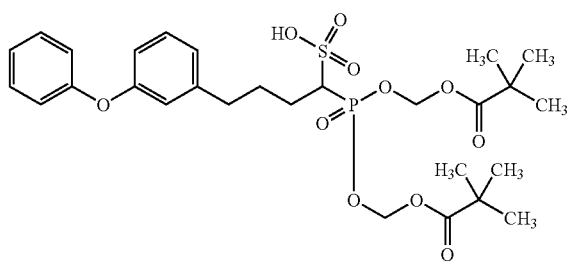

BMS-188494

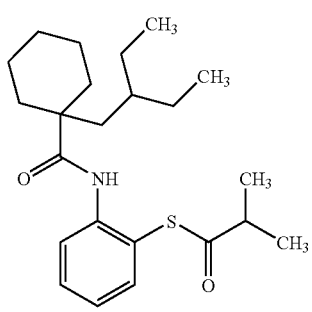

JTT-705

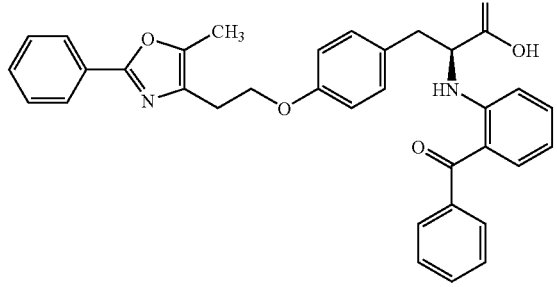

Gl 262570

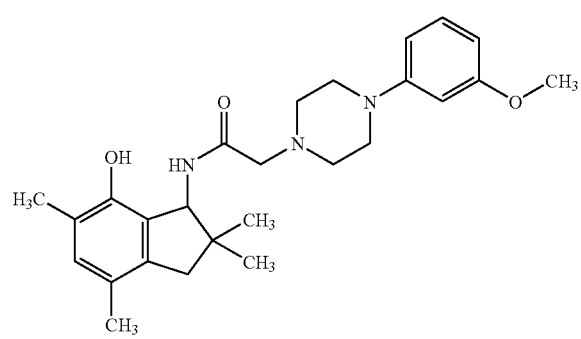

OPC-14117

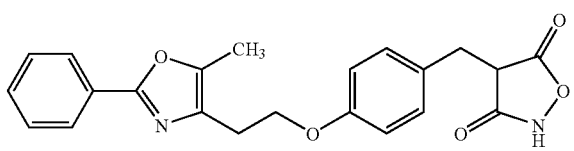

JTT-501

The examples detailed below serve to illustrate the invention without, however, restricting it.

TABLE 1

Compounds of the formula Ib

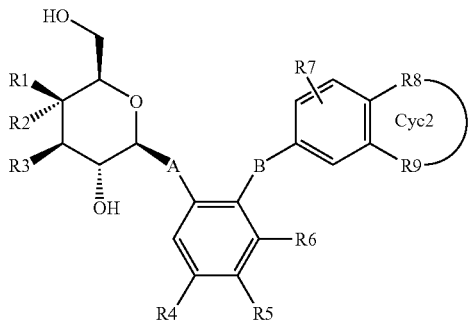

Ib

| Ex. | R1 | R2 | R3 | R4, R5, R6 | R7 | R8, R9 | A | B | Cyc1 | Cyc2 | MS* |
|---|---|---|---|---|---|---|---|---|---|---|---|
| 1  | H | F | OH | H, H, H       | H | O—$CH_3$, H       | O | $CH_2$           | Phenyl |         | Ok |
| 2  | H | F | OH | H, H, H       | H | H, H              | O | $CH_2$           | Phenyl |         | Ok |
| 3  | F | H | OH | H, H, H       | H | O—$CH_3$, H       | O | $CH_2$           | Phenyl |         | Ok |
| 4  | H | F | OH | $CH_3$, H, OH | H | —CH=CH—O—         | O | CO—$CH_2$—$CH_2$ | Phenyl | Furenyl | Ok |
| 5  | F | H | OH | $CH_3$, H, OH | H | —CH=CH—O—         | O | CO—$CH_2$—$CH_2$ | Phenyl | Furenyl | Ok |
| 6  | F | H | OH | $CH_3$, H, OH | H | —$CH_2$—$CH_2$—O— | O | CO—$CH_2$—$CH_2$ | Phenyl | Furanyl | Ok |
| 7  | H | F | OH | $CH_3$, H, OH | H | O—$CH_3$, H       | O | CO—$CH_2$—$CH_2$ | Phenyl |         | Ok |
| 8  | H | F | OH | $CH_3$, H, OH | H | OH, H             | O | CO—$CH_2$—$CH_2$ | Phenyl |         | Ok |
| 9  | H | F | OH | OH, H, OH     | H | OH, H             | O | CO—$CH_2$—$CH_2$ | Phenyl |         | Ok |
| 10 | F | H | OH | OH, H, OH     | H | OH, H             | O | CO—$CH_2$—$CH_2$ | Phenyl |         | Ok |
| 11 | H | F | OH | H, H, OH      | H | H, H              | O | CO—NH—$CH_2$     | Phenyl |         | Ok |
| 12 | F | H | OH | H, H, OH      | H | O—$CH_3$, H       | O | CO—NH—$CH_2$     | Phenyl |         | Ok |
| 13 | H | F | OH | $CH_3$, H, OH | H | O—$CH_3$, H       | O | CO—NH—$CH_2$     | Phenyl |         | Ok |
| 14 | F | H | OH | $CH_3$, H, OH | H | O—$CH_3$, H       | O | CO—NH—$CH_2$     | Phenyl |         | Ok |
| 15 | H | F | OH | $CH_3$, H, OH | H | $CH_2CH_3$, H     | O | CO—$CH_2$—$CH_2$ | Phenyl |         | Ok |
| 16 | H | F | OH | $CH_3$, H, OH | H | $CH_3$, H         | O | CO—$CH_2$—$CH_2$ | Phenyl |         | Ok |
| 17 | H | F | OH | $CH_3$, H, OH | H | $OCF_3$, H        | O | CO—$CH_2$—$CH_2$ | Phenyl |         | Ok |
| 18 | H | F | OH | $CH_3$, H, OH | H | Cl, H             | O | CO—$CH_2$—$CH_2$ | Phenyl |         | Ok |
| 19 | F | F | OH | H, H, H       | H | H, H              | O | $CH_2$           | Phenyl |         | Ok |
| 20 | H | F | OH | H, H, H       | H | $CH_2CH_3$, H     | O | $CH_2$           | Phenyl |         | Ok |
| 21 | H | F | OH | $OCH_3$, H, H | H | O—$CH_3$, H       | O | $CH_2$           | Phenyl |         | Ok |
| 22 | H | F | OH | H, F, H       | H | O—$CH_3$, H       | O | $CH_2$           | Phenyl |         | Ok |
| 23 | H | F | OH | H, $OCH_3$, H | H | $CH_2CH_3$, H     | O | $CH_2$           | Phenyl |         | Ok |
| 24 | H | F | OH | H, H, H       | H | $CH_2CH_3$, H     | O | O                | Phenyl |         | Ok |

*The indication "MS is ok" means that a mass spectrum or HPLC/MS was recorded and the molecular peak ($MH^+$) and/or M + 18 ($MNH_4^+$) and/or M + 23 ($MNa^+$) was detected therein The compounds of the formula I are distinguished by beneficial effects on glucose metabolism; in particular, they lower the blood glucose level and are suitable for the treatment of type 1 and type 2 diabetes. The compounds can therefore be employed alone or in combination with other blood glucose-lowering active ingredients (antidiabetics).

The compounds of the formula I are further suitable for the prevention and treatment of late damage from diabetes, such as, for example, nephropaty, retinopathy, neuropathy and syndrome X, obesity, myocardial infarct, myocardial infarction, peripheral arterial occlusive diseases, thromboses, arteriosclerosis, inflammations, immune diseases, autoimmune diseases such as, for example, AIDS, asthma, osteoporosis, cancer, psoriasis, Alzheimer's, schizophrenia and infectious diseases, with preference for the treatment of type 1 and type 2 diabetes and the prevention and treatment of late damage from diabetes, syndrome X and obesity.

The activity of the compounds was tested as follows:

Preparation of brush border membrane vesicles from the small intestine of rabbits, rats and pigs Preparation of brush border membrane vesicles from the intestinal cells of the small intestine was carried out by the so-called $Mg^{2+}$ precipitation method. The mucosa of the small intestine was scraped off and suspended in 60 ml of ice-cold Tris/HCl buffer (ph 7.1)/300 mM mannitol, 5 mM EGTA. Dilution to 300 ml with ice-cold distilled water was followed by homogenization with an Ultraturrax (18 shaft, IKA Werk Staufen, FRG) at 75% of the max. power for 2×1 minute, while cooling in ice. After addition of 3 ml of 1M $MgCl_2$ solution (final concentration 10 mM), the mixture is left to stand at 0° C. for exactly 15 minutes. Addition of $Mg^{2+}$ causes the cell membranes to aggregate and precipitate with the exception of the brush border membranes. After centrifugation at 3 000×g (5 000 rpm, SS-34 rotor) for 15 minutes, the precipitate is discarded and the supernatant, which contains the brush border membranes, is centrifuged at 26 700×g (15 000 rpm, SS-34 rotor) for 30 minutes. The supernatant is discarded, and the precipitate is rehomogenized in 60 ml of 12 mM Tris/HCl buffer (ph 7.1)/60 mM mannitol, 5 mM EGTA using a Potter Elvejhem homogenizer (Braun, Melsungen, 900 rpm, 10 strokes). Addition of 0.1 ml of 1M $MgCl_2$ solution and incubation at 0° C. for 15 minutes is followed by centrifugation again at 3 000×g for 15 minutes. The supernatant is then centrifuged again at 46 000×g (20 000 rpm, SS-34 rotor) for 30 minutes. The precipitate is taken up in 30 ml of 20 mM Tris/Hepes buffer (pH 7.4)/280 mM mannitol and homogeneously resuspended by 20 strokes in a Potter Elveihem homogenizer at 1 000 rpm. After centrifugation at 48 000×g (20 000 rpm, SS-34 rotor) for 30 minutes, the precipitate was taken up in 0.5 to 2 ml of Tris/Hepes buffer (pH 7.4)/280 mM mannitol (final concentration 20 mg/ml) and resuspended using a tuberculin syringe with a 27 gauge needle.

The vesicles were either used directly after preparation for labeling or transport studies or were stored at −196° C. in 4 mg portions in liquid nitrogen.

To prepare brush border membrane vesicles from rat small intestine, 6 to 10 male Wistar rats (bred at Kastengrund, Aventis Pharma) were sacrificed by cervical dislocation, and the small intestines were removed and rinsed with cold isotonic saline. The intestines were cut up and the mucosa was scraped off. The processing to isolate brush border membranes took place as described above. To remove cytoskeletal fractions, the brush border membrane vesicles from rat small intestine were treated with KSCN as chaotropic ion.

To prepare brush border membranes from rabbit small intestine, rabbits were sacrificed by intravenous injection of 0.5 ml of an aqueous solution of 2.5 mg of tetracaine HCl, 100 mg of m-butramide and 25 mg of mebezonium iodide. The small intestines were removed, rinsed with ice-cold physiological saline and stored frozen in plastic bags under nitrogen at −80° C. and 4 to 12 weeks. For preparation of the membrane vesicles, the frozen intestines were thawed at 30° C. in a water bath and then the mucosa was scraped off. Processing to give membrane vesicles took place as described above.

To prepare brush border membrane vesicles from pig intestine, jejunum segments from a freshly slaughtered pig were rinsed with ice-cold isotonic saline and frozen in plastic bags under nitrogen at −80° C. Preparation of the membrane vesicles took place as described above.

Preparation of Brush Border Membrane Vesicles from the Renal Cortex of the Rat Kidney Brush border membrane vesicles were prepared from the cortex of the rat kidney by the method of Biber et al. The kidneys from 6 to 8 rats (200 to 250 g) were removed and the cortex was cut off each kidney as a layer about 1 mm thick. The kidneys were taken up in 30 ml of ice-cold 12 mM Tris/HCl buffer (pH 7.4)/300 mM mannitol and homogenized with an Ultraturrax shaft (level 180 V) for 4×30 seconds while cooling in ice. Addition of 42 ml of ice-cold distilled water was followed by addition of 850 µl of a 1M $MgCl_2$ solution. Incubation at 0° C. for 15 minutes was followed by centrifugation at 4 500 rpm (Sorvall SS-34 rotor) for 15 minutes. The precipitate was discarded, and the supernatant was centrifuged at 16 000 rpm for 30 minutes. Resuspension of the precipitate in 60 ml of 6 mM Tris/HCl buffer (pH 7.4)/150 mM mannitol/2.5 mM EGTA by 10 strokes in a Potter-Elvejhem homogenizer (900 rpm) and addition of 720 µl of 1 mM $MgCl_2$ solution was followed by incubation at 0° C. for 15 minutes. The supernatant resulting after centrifugation at 4 500 rpm (SS-34 rotor) for 15 minutes was centrifuged at 16 000 rpm for 30 minutes. The supernatant was homogenized by 10 strokes in 60 ml of 20 mM Tris/Hepes buffer (pH 7.4)/280 mM mannitol, and the resulting suspension was then centrifuged at 20 000 rpm for 30 minutes. The precipitate was resuspended in 20 mM Tris/HCl buffer (pH 7.4)/280 mM mannitol using a tuberculin syringe with a 27 gauge needle and was adjusted to a protein concentration of 20 mg/ml.

Measurement of the Glucose Uptake by Brush Border Membrane Vesicles

The uptake of [$^{14}$C]-labeled glucose into brush border membrane vesicles was measured by the membrane filtration method. 10 µl of the brush border membrane vesicle suspension in 10 mM Tris/Hepes buffer (pH 7.4)/300 mM mannitol were added at 30° C. to 90 µl of a solution of 10 µM [$^{14}$C]D-glucose and the appropriate concentrations of the relevant inhibitors (5-200 µM) in 10 mM Tris/Hepes buffer (pH 7.4)/100 mM NaCl/100 mM mannitol.

After incubation for 15 seconds, the transport process was stopped by adding 1 ml of ice-cold stop solution (10 mM Tris/Hepes buffer (pH 7.4)/150 mM KCl) and the vesicle suspension was immediately filtered with suction through a cellulose nitrate membrane filter (0.45 µm, 25 mm diameter, Schleicher & Schüll) under a vacuum of from 25 to 35 mbar. The filter was washed with 5 ml of ice-cold stop solution. Each measurement was carried out as duplicate or triplicate determination. To measure the uptake of radiolabeled substrates, the membrane filter was dissolved in 4 ml of an appropriate scintillator (Quickszint 361, Zinsser Analytik GmbH, Frankfurt am Main), and the radioactivity was determined by liquid scintillation measurement. The measured values were obtained as dpm (decompositions per minute) after calibration of the instrument using standard samples and after correction for any chemiluminescence present.

The active ingredients are compared for activity on the basis of $IC_{25}$ data obtained in the transport assay on rabbit small intestine brush border membrane vesicles for selected substances. (The absolute values may be species- and experiment-dependent)

| Example No. | IC50 [µM] |
|---|---|
| Phlorizin | 16 |
| 1 | 0.5 |
| 2 | 0.7 |
| 4 | 1.5 |
| 5 | 0.4 |
| 7 | 0.9 |

The preparation of various examples is described in detail below, and the other compounds of the formula I were obtained analogously:

EXPERIMENTAL PART

Reaction Scheme: Synthesis of α-bromoglycosides

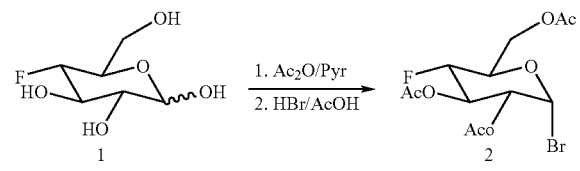

-continued

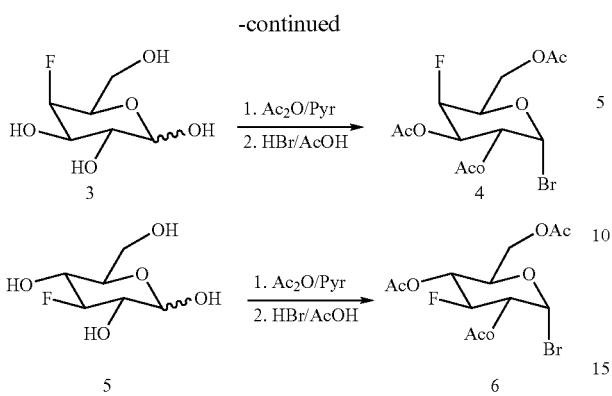

1-Bromo-4-deoxy-4-fluoro-2,3,6-tri-O-acetyl-alpha-D-glucose 2

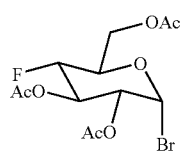

5 g (27.5 mmol) of 4-deoxy-4-fluoro-D-glucopyranose 1 (Apollo) are suspended in 50 ml of pyridine and 50 ml of acetic anhydride. The reaction solution is stirred at 45° C. for 4 hours. This results in a clear reaction solution which is then concentrated. 12 g of crude product are obtained. This crude product is dissolved in 160 ml of 33% strength HBr in glacial acetic acid and left to stand at room temperature for 2 hours. The reaction solution is then poured into a mixture of 300 g of ice and 300 ml of ethyl acetate. The organic phase is washed twice more with aqueous NaCl solution, filtered through a little silica gel and concentrated. The residue is separated by chromatography on silica gel (ethyl acetate/heptane=1/1). 8.19 g (80% over 2 stages) of 2 are obtained as a pale yellow solid.

1-Bromo-4-deoxy-4-fluoro-2,3,6-tri-O-acetyl-alpha-D-galactose 4

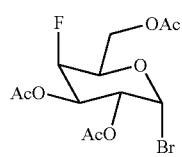

100 mg (0.55 mmol) of 3 are reacted with 3.5 ml of pyridine and 3.5 ml of acetic anhydride in analogy to the preparation of compound 2. 89 mg (44%) of 4 are obtained as an amorphous solid.

1-Bromo-3-deoxy-3-fluoro-2,4,6-tri-O-acetyl-alpha-D-glucose 6

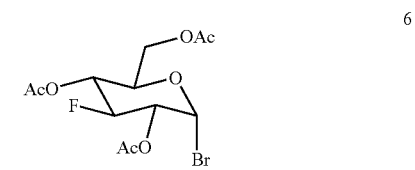

335 mg (1.84 mmol) of 5 are reacted with 10 ml of pyridine and 10 ml of acetic anhydride in analogy to the preparation of compound 2. 628 mg (92%) of 6 are obtained as an amorphous solid.

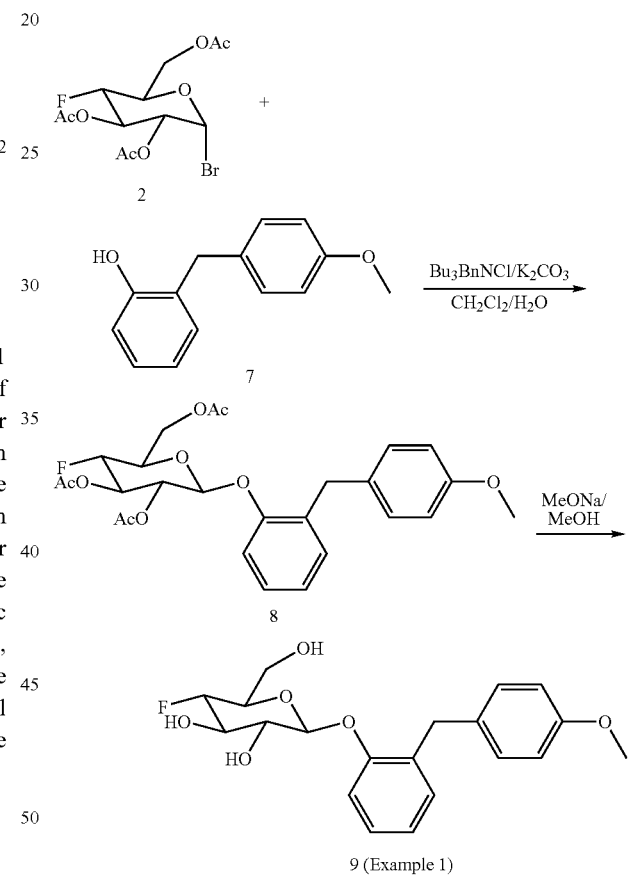

The following were prepared in an analogous manner:

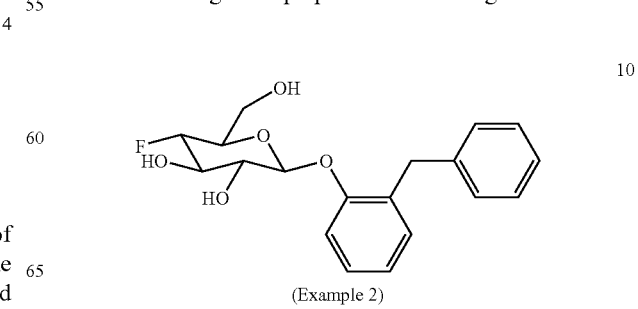

-continued

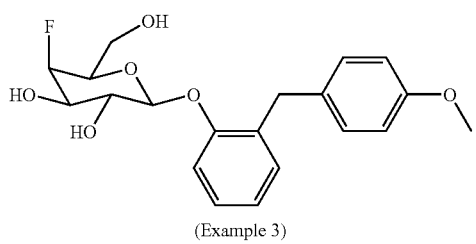

(Example 3)

Example 1

Compound 9

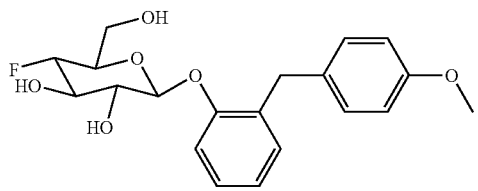

9

100 mg (0.47 mmol) of 2-(4-methoxybenzyl)phenol 7 and 370 mg (1.17 mmol) of bromide 2 are dissolved in 6 ml of metylene chloride. 160 mg of Bu$_3$BnNCl (PTC=phase transfer catalyst), 320 mg of K$_2$CO$_3$ and 0.4 ml of water are successively added to this solution, which is then stirred at room temperature for 20 hours. The reaction solution is diluted with 20 ml of ethyl acetate and filtered through silica gel. The filtrate is concentrated and the residue is separated by chromatography on silica gel (ethyl acetate/heptane=1/1). 72 mg of 8 are obtained as a colorless solid. The resulting 72 mg of 8 are taken up in 4 ml of methanol, and 1 ml of 1 N NaOMe/MeOH is added. After one hour, the mixture is neutralized with methanolic HCl and concentrated, and the residue is separated by chromatography on silica gel (methylene chloride/methanol/conc. ammonia, 30/5/1). 29 mg of 9 are obtained as a colorless solid. $C_{20}H_{23}FO_6$ (378.40) MS(ESI$^-$) 423.22 (M+CHO$_2^-$).

Example 2

Compound 10

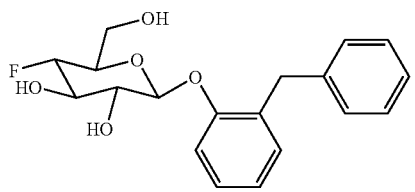

10

100 mg (0.47 mmol) of 2-benzylphenol and 370 mg (1.17 mmol) of bromide 2 are reacted in analogy to the synthesis of compound 9, and 31 mg of 10 are obtained as a colorless solid. $C_{19}H_{21}FO_5$ (348.37) MS(ESI$^-$) 393.15 (M+CHO$_2^-$).

Example 3

Compound 11

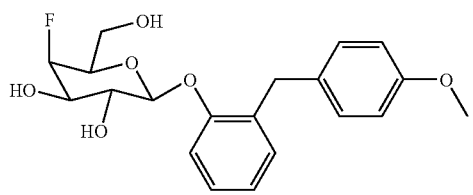

11

200 mg (0.94 mmol) of 2-(4-methoxybenzyl)phenol 7 and 200 mg (0.63 mmol) of bromide 4 are reacted in analogy to the synthesis of compound 9, and 110 mg of 11 are obtained as a colorless solid. $C_{20}H_{23}FO_6$ (378.40) MS(ESI$^-$) 423.22 (M+CHO$_2^-$).

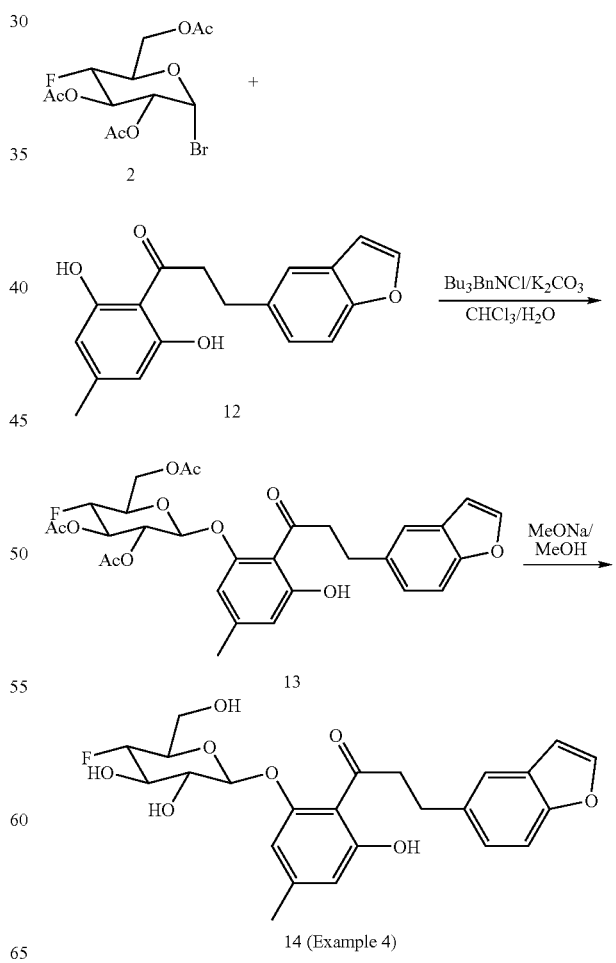

14 (Example 4)

The following were prepared in an analogous manner:

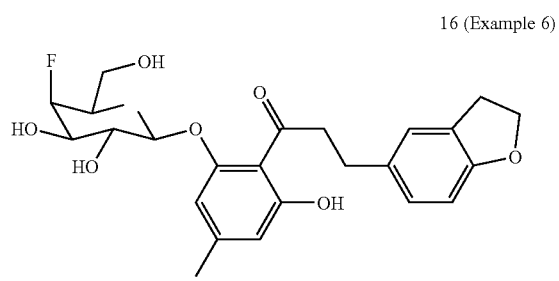

16 (Example 6)

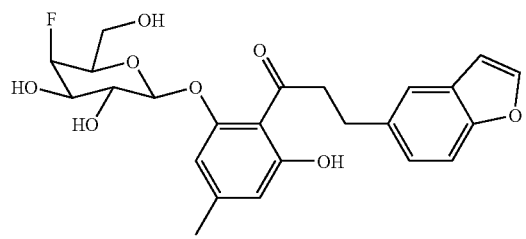

15 (Example 5)

Example 4

Compound 14

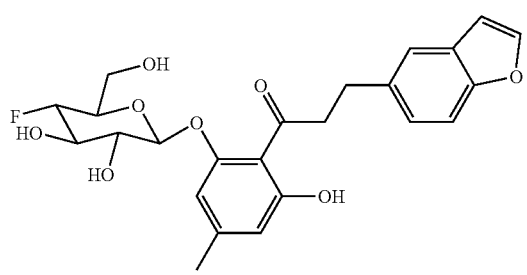

90 mg (0.30 mmol) of 3-benzofuran-5-yl-1-(2,6-dihydroxy-4-methylphenyl)propan-1-one 12 and 280 mg (0.76 mmol) of bromide 2 are reacted in analogy to the synthesis of compound 8, and 400 mg of 13 are obtained as crude product which is directly deprotected with NaOMe/MeOH in analogy to the synthesis of glucoside 9. 75 mg of 14 (54% over 2 stages) are obtained as a colorless solid. $C_{24}H_{25}FO_8$ (460.46) MS(ESI$^-$) 459.03 (M–H$^+$).

Example 5

Compound 15

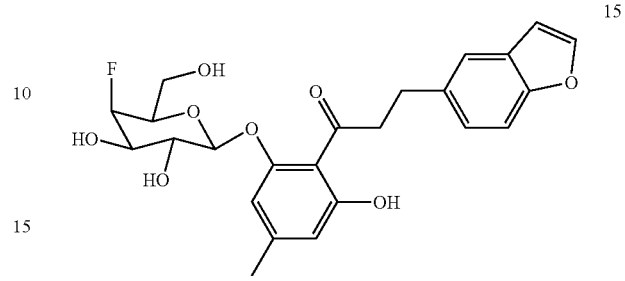

100 mg (0.33 mmol) of 3-benzofuran-5-yl-1-(2,6-dihydroxy-4-methylphenyl)propan-1-one 12 and 150 mg (0.40 mmol) of bromide 4 are reacted in analogy to the synthesis of compound 14, and 75 mg of 15 are obtained as a colorless solid. $C_{24}H_{25}FO_8$ (460.46) MS(ESI$^-$) 459.03 (M–H$^+$).

Example 6

Compound 16

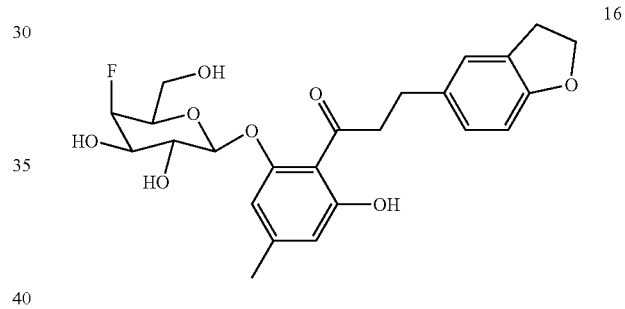

150 mg (0.5 mmol) of 3-(2,3-dihydroxybenzofuran-5-yl-1-(2,6-dihydroxy-4-methylphenyl)propan-1-one and 150 mg (0.40 mmol) of bromide 4 are reacted in analogy to the synthesis of compound 14, and 75 mg of 16 are obtained as a colorless solid. $C_{24}H_{27}FO_8$ (462.46) MS(ESI$^-$) 461.03 (M–H$^+$).

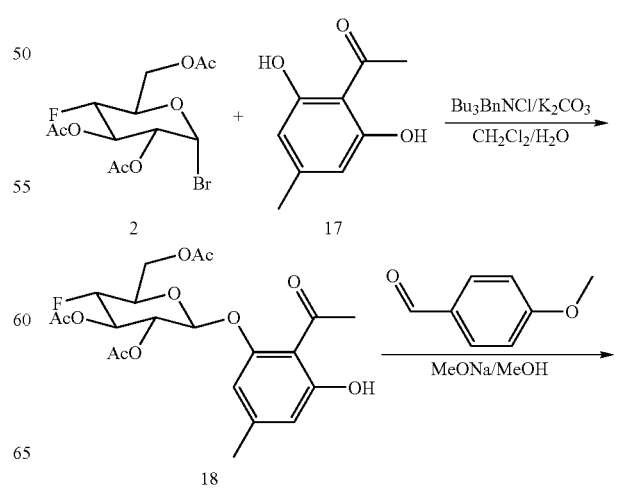

-continued

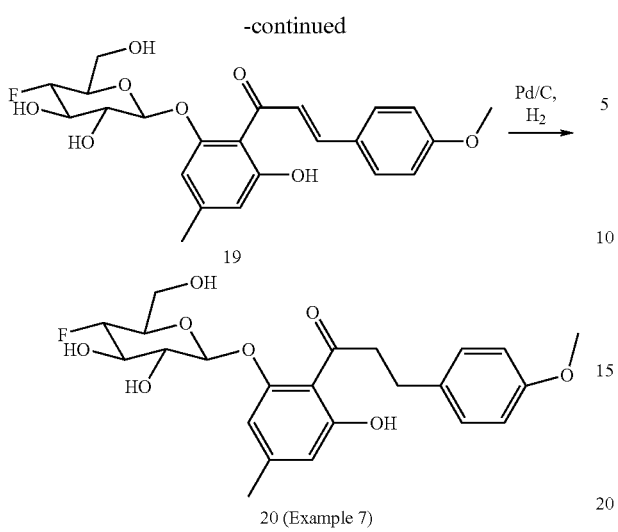

20 (Example 7)

The following was prepared in an analogous manner:

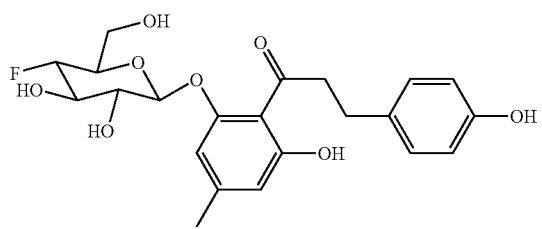

21 (Example 8)

Example 7

Compound 20

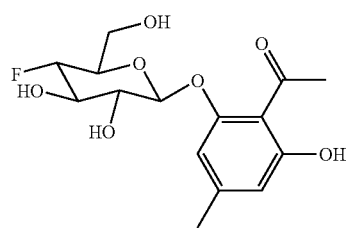

1.0 g (6.0 mmol) of 1-(2,6-dihydroxy-4-methylphenyl) ethanone 17 and 1.0 g (2.7 mmol) of bromide 2 are dissolved in 30 ml of methylene chloride. 800 mg of benzyltributylammonium chloride (PTC), 1.6 g of potassium carbonate and 1.5 ml of water are successively added to this solution while stirring vigorously. This suspension is stirred with protection from light (aluminum foil) for 18 hours and then diluted with 150 ml of ethyl acetate and 150 ml of n-heptane. The solid constituents are filtered through a little silica gel and concentrated. The residue is separated by chromatography on silica gel (ethyl acetate/heptane=1/2). 430 mg of 18 are obtained as a pale yellow solid (can be separated with difficulty from an identically migrating byproduct, and thus the purity is only about 50%. The byproduct can easily be removed at the next stage). $C_{21}H_{25}O_{10}F$ (456.43) MS(ESI$^-$): 455.25 (M–H$^+$).

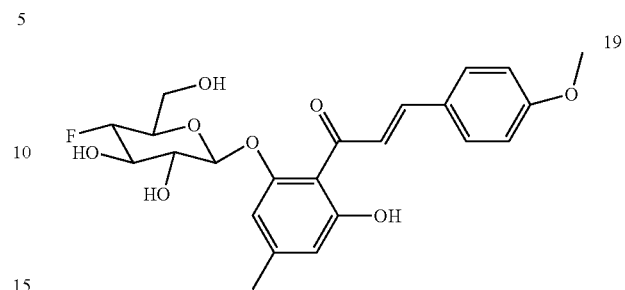

200 mg of compound 18 (about 50% pure) and 225 mg of anisaldehyde (Fluka) are dissolved in 10 ml of methanol. After addition of 5 ml of 1 N NaOMe/MeOH solution, the reaction solution is boiled under reflux for 12 hours. The reaction solution is neutralized with methanolic HCl and concentrated, and the residue is separated by chromatography on silica gel (methylene chloride/methanol/conc. ammonia, 30/5/1). 60 mg of 19 are obtained as a yellow solid.

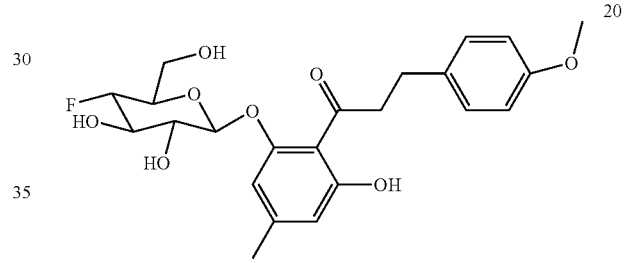

60 mg (0.13 mmol) of chalcone 19 and 50 mg of Pd/C (10% Pd) are suspended in 15 ml of methanol and hydrogenated under a 5 bar hydrogen atmosphere at room temperature for 5 h. The reaction solution is concentrated and the residue is purified by flash chromatography (methylene chloride/methanol/conc. ammonia, 30/5/1).

Yield 25 mg (42%) of 20 as a white amorphous solid. $C_{23}H_{27}FO_8$ (424.47) MS(ESI$^-$): 449.17 (M–H$^+$).

Example 8

Compound 21

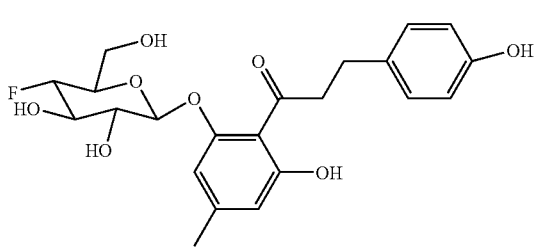

200 mg of compound 18 (about 50% pure) and 350 mg of p-benzyloxybenzaldehyde (Fluka) are reacted in analogy to the synthesis of compound 20. 36 mg of 21 are obtained as a colorless solid. $C_{22}H_{25}FO_8$ (436.44) MS(ESI⁻) 481.08 (M+CHO₂⁻).

350 mg of bromide 2, 100 mg of phenol 22 and 350 mg of p-benzyloxybenzaldehyde (Fluka) are reacted in analogy to the synthesis of compound 21. 40 mg of 27 are obtained as a colorless solid. $C_{21}H_{23}FO_9$ (438.41) MS(ESI⁻) 483.15 (M+CHO₂⁻).

Example 10

Compound 28

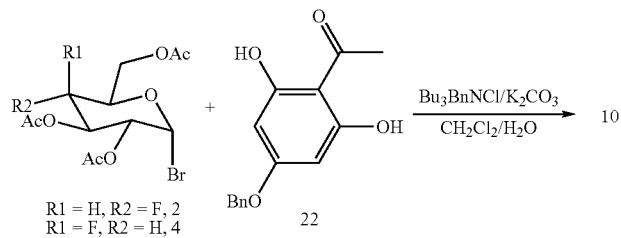

R1 = H, R2 = F, 2
R1 = F, R2 = H, 4

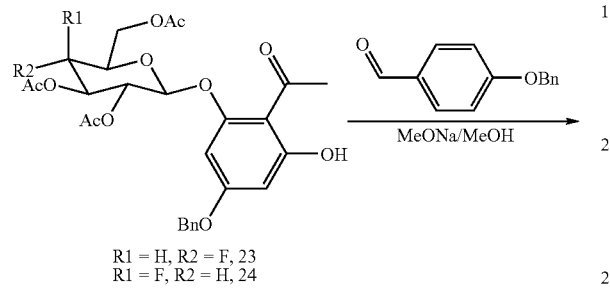

R1 = H, R2 = F, 23
R1 = F, R2 = H, 24

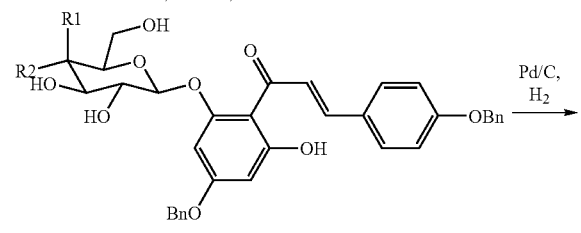

R1 = H, R2 = F, 25
R1 = F, R2 = H, 26

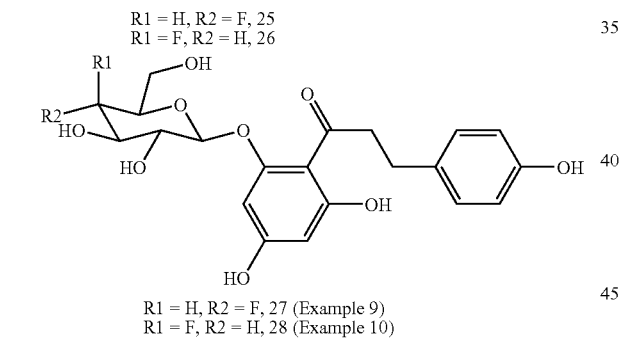

R1 = H, R2 = F, 27 (Example 9)
R1 = F, R2 = H, 28 (Example 10)

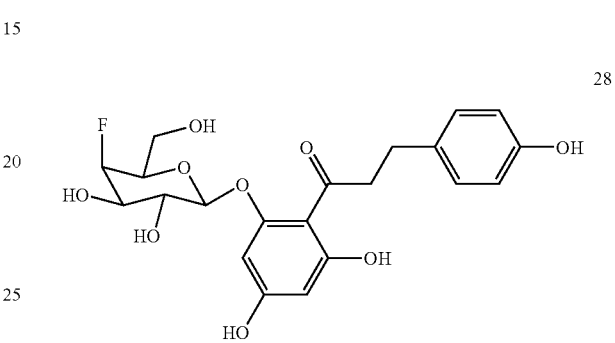

110 mg of bromide 4 80 mg of phenol 22 and 350 mg of p-benzyloxybenzaldehyde (Fluka) are reacted in analogy to the synthesis of compound 21. 50 mg of 28 are obtained as a colorless solid. $C_{21}H_{23}FO_9$ (438.41) MS(ESI⁻) 483.15 (M+CHO₂⁻).

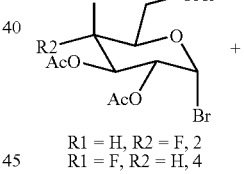

R1 = H, R2 = F, 2
R1 = F, R2 = H, 4

Example 9

Compound 27

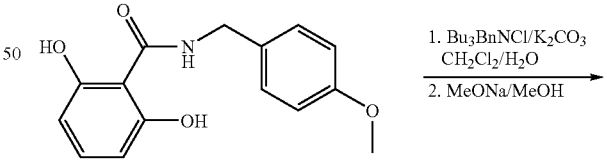

29

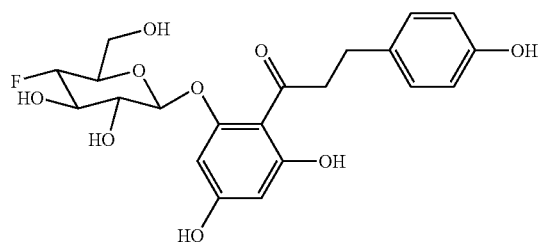

27

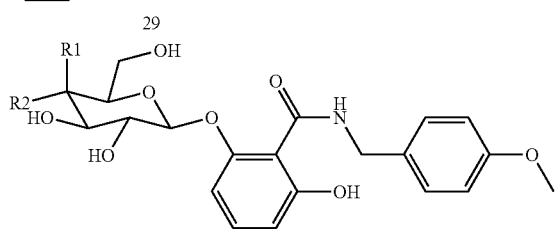

R1 = H, R2 = F, 30 (Example 11)
R1 = F, R2 = H, 31 (Example 12)

Example 11

Compound 30

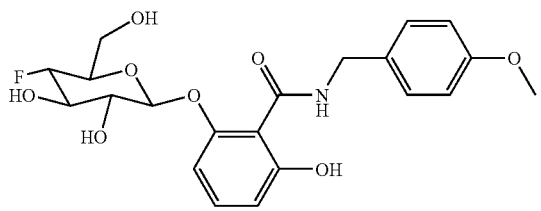

200 mg of bromide 2 and 300 mg of phenol 29 are reacted in analogy to the synthesis of compound 14. 40 mg of 30 are obtained as a colorless solid. $C_{21}H_{24}FNO_8$ (437.43) MS(ESI$^-$) 482.15 (M+CHO$_2^-$).

Example 12

Compound 31

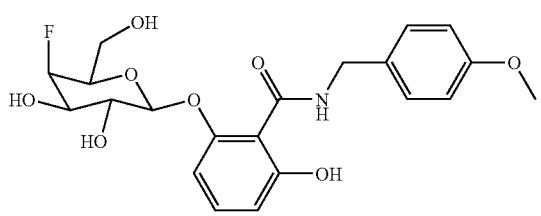

200 mg of bromide 4 and 300 mg of phenol 29 are reacted in analogy to the synthesis of compound 14. 115 mg of 31 are obtained as a colorless solid. $C_{21}H_{24}FNO_8$ (437.43) MS(ESI$^-$) 482.15 (M+CHO$_2^-$).

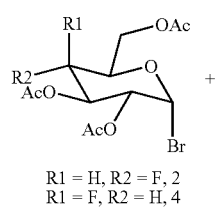

R1 = H, R2 = F, 2
R1 = F, R2 = H, 4

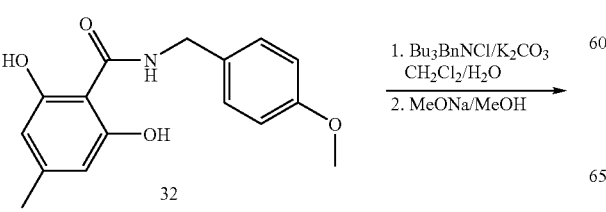

1. Bu$_3$BnNCl/K$_2$CO$_3$ CH$_2$Cl$_2$/H$_2$O
2. MeONa/MeOH

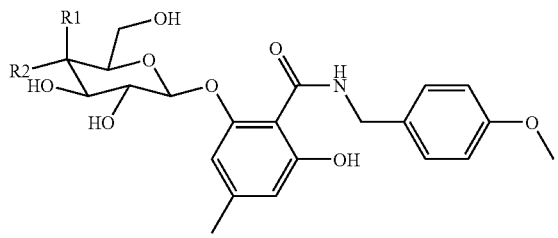

R1 = H, R2 = F, 33 (Example 13)
R1 = F, R2 = H, 34 (Example 14)

Example 13

Compound 33

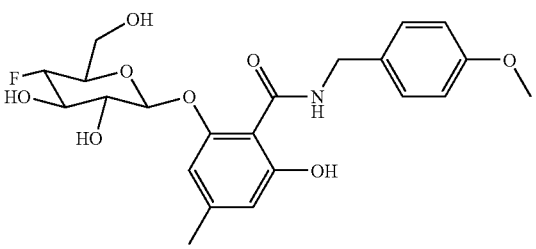

200 mg of bromide 2 and 300 mg of phenol 32 are reacted in analogy to the synthesis of compound 14. 80 mg of 33 are obtained as a colorless solid. $C_{22}H_{26}FNO_8$ (451.45) MS(ESI$^-$) 496.17 (M+CHO$_2^-$).

Example 14

Compound 34

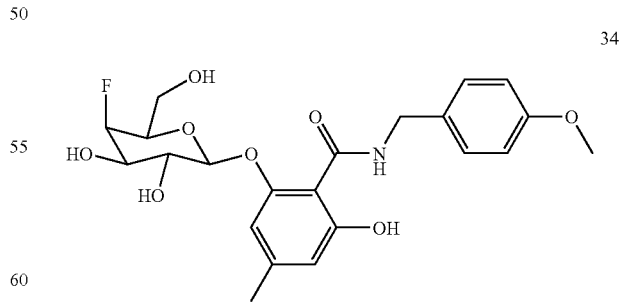

200 mg of bromide 4 and 300 mg of phenol 32 are reacted in analogy to the synthesis of compound 14. 130 mg of 34 are obtained as a colorless solid. $C_{21}H_{24}FNO_8$ (451.45) MS(ESI$^-$) 496.15 (M+CHO$_2^-$).

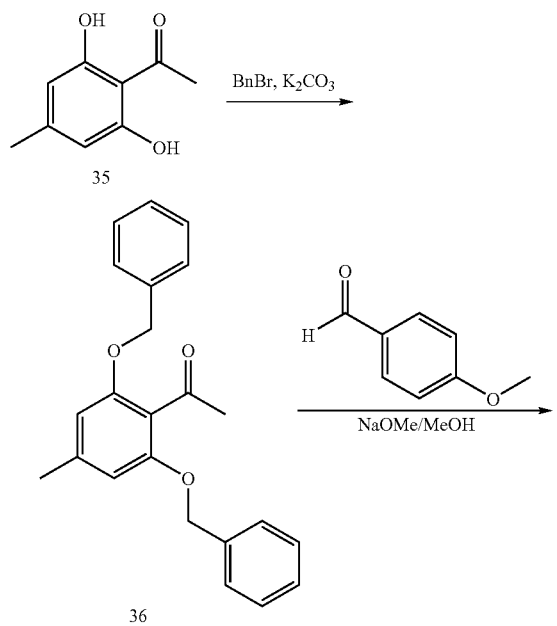

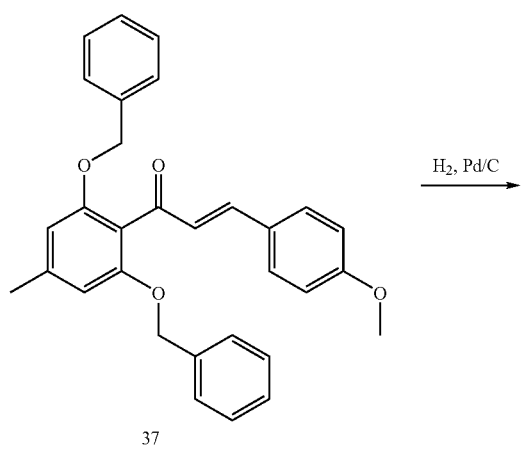

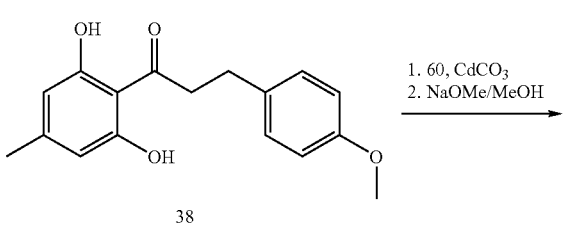

20 (Example 7)

1-(2,6-Bisbenzyloxy-4-methylphenyl)ethanone 36

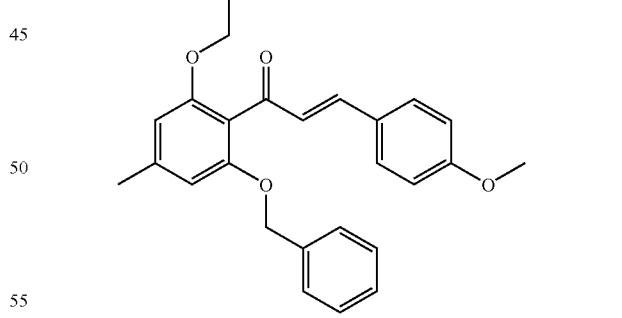

1.62 g (9.75 mmol) of 1-(2,6-dihydroxy-4-methylphenyl) ethanone (35) are dissolved in 30 ml of dimethylformamide, and 4.0 ml (33.7 mmol) of benzyl bromide and 13.8 g (100 mmol) of potassium carbonate are added. The reaction mixture is stirred at room temperature for 3 hours. This is followed by addition of water and extraction twice with ethyl acetate. The combined organic phases are washed with saturated sodium chloride solution, dried over sodium sulfate and concentrated in a rotary evaporator. 1.35 g (40%) of compound 36 are obtained as a colorless crystalline product. $C_{23}H_{22}O_3$ (346.2) MS (ESI$^+$): 347.15 (M+H$^+$).

1-(2,6-Bisbenzyloxy-4-methylphenyl)-3-(4-methoxyphenyl)propenone 37

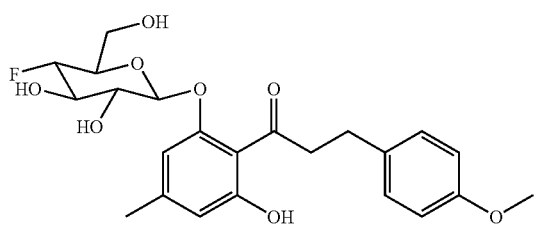

3.46 g (10 mmol) of 1-(2,6-bisbenzyloxy-4-methylphenyl)ethanone (36) are dissolved in 150 ml of ethanol, and 1.34 ml of p-anisaldehyde are added. 7 ml of aqueous potassium hydroxide solution are then added dropwise. The reaction stirs at room temperature for 12 hours.

Half of the solvent is stripped off in a rotary evaporator. The mixture is neutralized with 2 M hydrochloric acid while cooling in ice and is then extracted three times with water and ethyl acetate. The organic phases are combined, washed with saturated sodium chloride solution, dried over sodium sulfate and concentrated. The isolated oil crystallizes out. The crystals are stirred in diethyl ether, filtered off with suction and dried. 4.3 g (92%) of the compound 37 are obtained as a colorless solid. g/mol $C_{31}H_{28}O_4$ (464.2) MS (ESI$^+$): 465.10 (M+H$^+$).

1-(2,6-Dihydroxy-4-methylphenyl)-3-(4-methoxyphenyl)propan-1-one 38

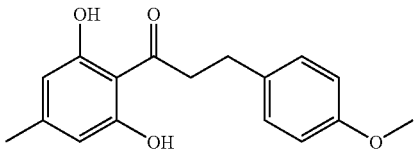

1.50 g (3.23 mmol) of 1-(2,6-bisbenzyloxy-4-methylphenyl)ethanone (37) are dissolved in 40 ml of ethyl acetate and, under an argon atmosphere, 400 mg of palladium on activated carbon, 10%, are added. Hydrogenation is carried out in a hydrogenation autoclave under 3 bar at room temperature for 2 hours. The catalyst is then filtered off and washed with ethyl acetate, and the resulting solution is concentrated in a rotary evaporator. The crude product is purified by column chromatography (SiO$_2$, ethyl acetate/n-heptane 1:3).

600 mg of the product 38 (65%) are isolated as a colorless solid. $C_{17}H_{18}O_4$ 286.3 MS (ESI$^+$): 287.10 (M+H$^+$).

Reference Example 7

Compound 20

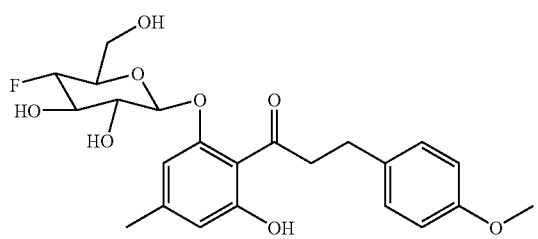

174.4 mg (0.61 mmol) of compound 38 are dissolved in 50 ml of toluene, and 340 mg (0.61 mmol) of the bromide 60 and 421 mg of cadmium carbonate (2.44 mmol) are added. The reaction mixture is refluxed with a water trap for 1 h. Cadmium carbonate is filtered off, and the resulting clear solution is concentrated in a rotary evaporator. The crude product is suspended in 25 ml of methanol and mixed with 5.0 ml of a 0.5 M methanolic NaOMe solution and stirred at room temperature for 12 h. The reaction solution is neutralized by adding methanolic HCl and is purified by flash chromatography (SiO$_2$, EtOAc/heptane 1:4→1:1). 78.8 mg (29%) of compound 20 are obtained as a colorless solid. $C_{23}H_{27}FO_8$ 450.5 MS (ESI$^+$): 473.15 (M+Na$^+$).

Compounds 40 (example 15), 41 (example 16), 42 (example 17) and 43 (example 18) were prepared in an analogous manner.

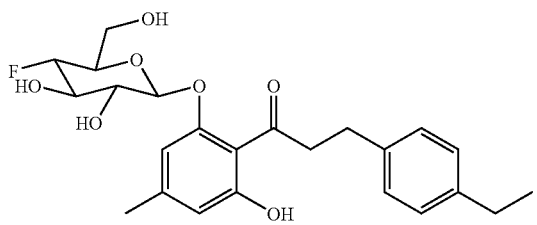

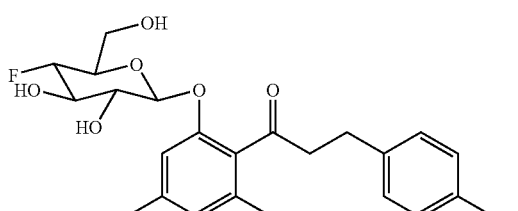

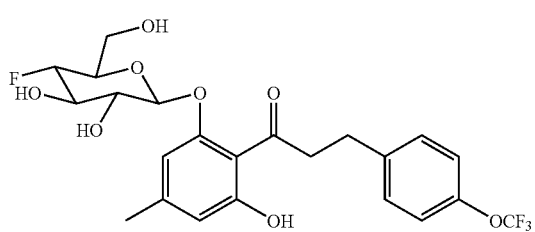

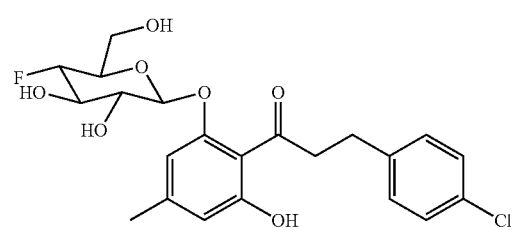

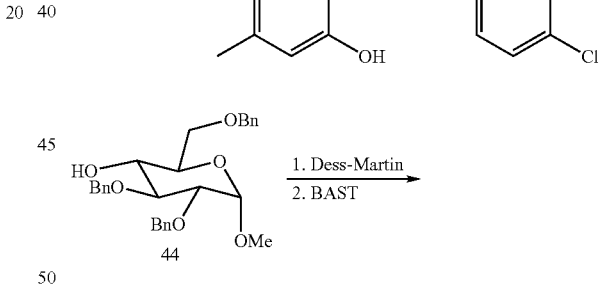

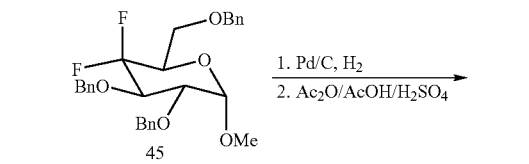

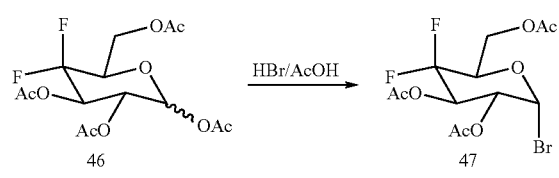

1-Methoxy-4-deoxy-4,4-difluoro-2,3,6-tri-O-benzyl-alpha-D-glucose 45

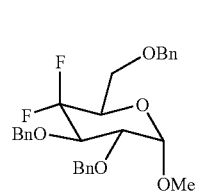

45

3.69 g (7.9 mmol) of 1-methoxy-2,3,6-tri-O-benzyl-α-D-glucose 44 (Tetrahedron Asymmetry 11 (2000) 385-387) are dissolved in 110 ml of methylene chloride and, under an argon atmosphere, 3.6 g (8.5 mmol) of Dess-Martin agent (Aldrich) are added dropwise. After 3 hours at room temperature, the mixture is diluted with 300 ml of ethyl acetate/n-heptane (1:1) and washed 1× with NaHCO$_3$ solution and 1× with Na$_2$S$_2$O$_3$ solution. The organic phase is filtered through silica gel and concentrated. The residue is separated by chromatography on silica gel (ethyl acetate/n-heptane 1:1). 2.9 g (79%) of ketone are obtained. The latter is dissolved in 30 ml of methylene chloride and, under an argon atmosphere, 4 ml of BAST (Aldrich) are added dropwise. After 20 hours at room temperature, the mixture is diluted with 200 ml of ethyl acetate and washed cautiously (strong effervescence) with cooled NaHCO$_3$ solution. The organic phase is filtered through silica gel and concentrated. The residue is separated by chromatography on silica gel (ethyl acetate/n-heptane 1:1). 2.6 g (85%) of 45 are obtained as a colorless oil.

4-Deoxy-4,4-difluoro-1,2,3,6-tetra-O-acetyl-alpha-D-glucose 46

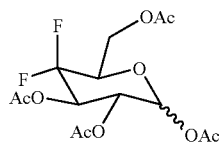

46

2.3 g (4.7 mmol) of 45 and 2 g of Pd/C (10% Pd) are dissolved in 150 ml of methanol and 10 ml of acetic acid and hydrogenated under an atmosphere of 5 bar of hydrogen at room temperature for 16 h. The reaction solution is concentrated and the residue is purified by flash chromatography (methylene chloride/methanol/conc. ammonia, 30/5/1). Yield 850 mg (83%) of 1-methoxy-4-deoxy-4,4-difluoro-alpha-D-glucose as white amorphous solid. C$_7$H$_{12}$F$_2$O$_5$ (214.17) MS(DCl): 215.4 (M+H$^+$). 700 mg (3.3 mmol) of this are dissolved in 3.5 ml of acetic acid and 6.3 ml of acetic anhydride. Addition of 0.2 ml of conc. H$_2$SO$_4$ is followed by stirring at 60° C. for 5 h. The reaction solution is then poured into a mixture of 30 g of ice and 30 ml of ethyl acetate. The organic phase is washed twice more with aqueous NaCl solution, filtered through a little silica gel and concentrated. The residue is separated by chromatography on silica gel (ethyl acetate/n-heptane 1:1). 300 mg (25%) of 46 are obtained as a mixture of anomers. C$_{14}$H$_{18}$F$_2$O$_9$ (368.29) MS(DCl): 369.3 (M+H$^+$).

1-Bromo-4-deoxy-4,4-difluoro-2,3,6-tri-O-acetyl-alpha-D-glucose 47

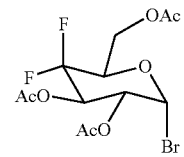

47

300 mg (0.8 mmol) of tetraacetate 46 are dissolved in 13 ml of 33% strength HBr in glacial acetic acid and left to stand at room temperature for 6 hours. The reaction solution is then poured into a mixture of 10 g of ice and 10 ml of ethyl acetate. The organic phase is washed twice more with aqueous NaCl solution, filtered through a little silica gel and concentrated. The residue is separated by chromatography on silica gel (ethyl acetate/heptane 1:1). 112 mg (35%) of 47 are obtained as a colorless solid. C$_{12}$H$_{15}$BrF$_2$O$_7$(389.15) MS(DCl): 389.2 (M+H$^+$).

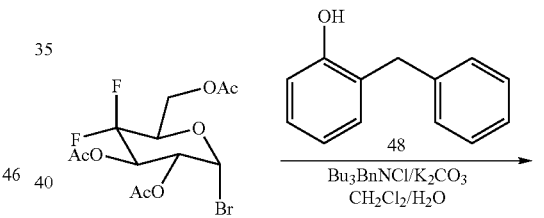

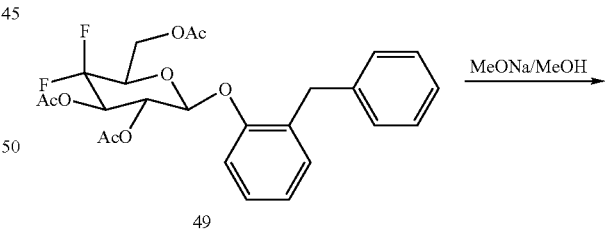

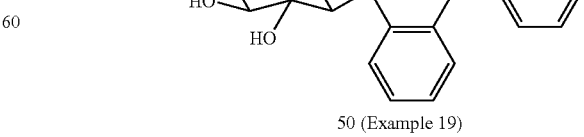

50 (Example 19)

Example 19

Compound 50

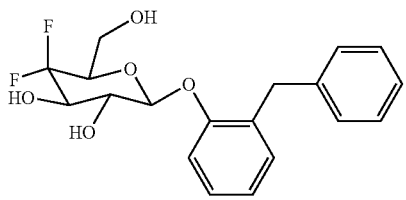

100 mg (0.47 mmol) of 2-benzylphenol (Aldrich) and 40 mg (0.10 mmol) of difluoro bromide 47 are reacted in analogy to the synthesis of compound 9, and 21 mg of 50 are obtained as a colorless solid. $C_{19}H_{20}F_2O_5$ (366.37) MS(ESI$^-$) 411.15 (M+CHO$_2^-$).

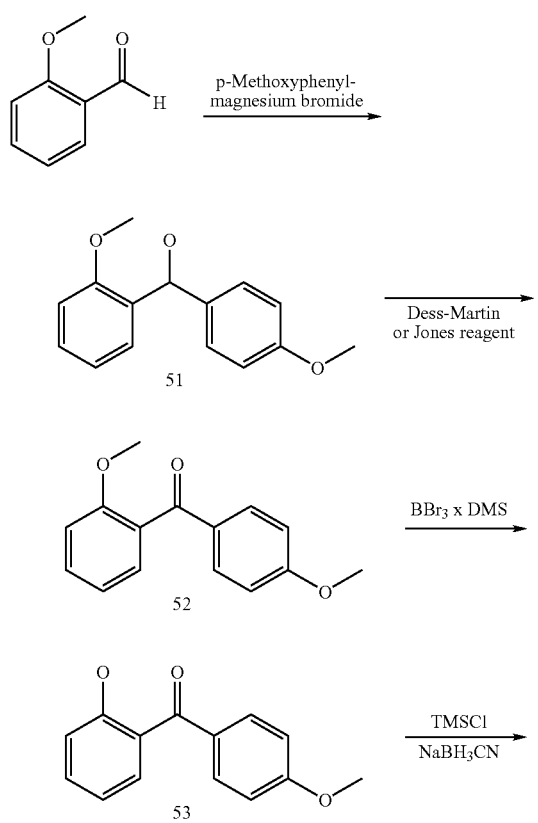

(4-Methoxyphenyl)-(2-methoxyphenyl)methanol 51

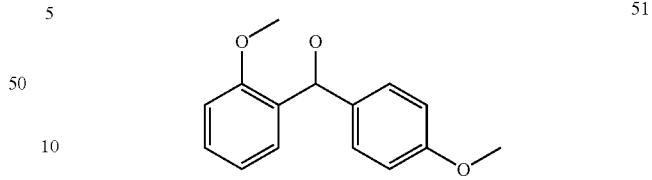

1.5 g of o-anisaldehyde are dissolved in THF and cooled to 0° C. 24.2 ml of 4-methoxyphenylmagnesium bromide (0.5 M in THF) are added to the mixture. The reaction solution is stirred at room temperature overnight and then poured into a 20% NH$_4$Cl solution and extracted with ethyl acetate. 2.63 g of the product are obtained, and this can be employed without further purification. $C_{15}H_{16}O_3$ (244.29) MS (ESI$^+$) 227.05 (M–OH)$^+$ (4-Methoxyphenyl)-(2-methoxyphenyl)methanone 52

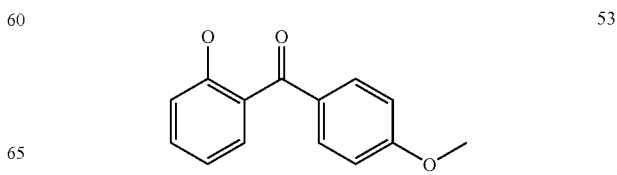

2.63 g of (4-methoxyphenyl)(2-methoxyphenyl)methanol 51 are dissolved in dichloromethane, and 5.03 g of Dess-Martin reagent are added. The mixture is stirred at room temperature for 2 h. Then 20% Na$_2$SO$_3$ and NaHCO$_3$ solution are added, and the mixture is extracted with diethyl ether. The organic phase is extracted with saturated NaCl solution and dried over sodium sulfate. The solution is concentrated in vacuo and purified by column filtration. 2.61 g of 52 are obtained. $C_{15}H_{14}O_3$ (242.28) MS (ESI$^+$) 243.04 (M+H$^+$)

Oxidation with Jones Reagent can take Place as an Alternative thereto:

155 mg of (4-methoxyphenyl)(2-methoxyphenyl)methanol 51 are dissolved in 10 ml of acetone, and 2 ml of Jones reagent are added dropwise. After 2 h at room temperature, 50 l of MTB ether and 30 ml of water are added to the mixture. The organic phase is washed several times with water, and the organic phase is extracted with saturated NaCl solution, dried over sodium sulfate and evaporated to dryness. The product (126 mg) obtained in this way has sufficient purity for further reaction.

(2-Hydroxyphenyl)(4-methoxyphenyl)methanone 53

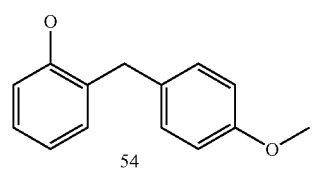

2.61 g of (4-methoxyphenyl)(2-methoxyphenyl)methanone 52 are dissolved in dichloromethane. The mixture is cooled in an ice bath, and 3.71 g of boron tribromide-dimethyl sulfide complex are added. The mixture is warmed to room temperature and left to stir for 3 h. The reaction is then stopped by pouring into ice-water, the dichloromethane phase is separated off, and the aqueous phase is extracted several times with ethyl acetate. The combined organic phase is washed with water and sodium chloride solution, dried over sodium sulfate and concentrated. The crude product is chromatographed on silica gel with ethyl acetate/heptane. 1.26 g of the product are obtained. $C_{14}H_{12}O_3$ (228.25) MS (DCI) 229.2 (M+H$^+$)

2-(4-Methoxybenzyl)phenol 7

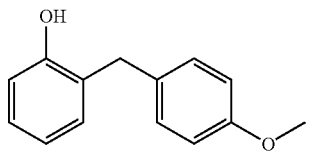

7

0.78 g of (2-hydroxyphenyl)(4-methoxyphenyl)methanone is dissolved in acetonitrile and cooled to 0° C. 2 ml of TMSCl are added dropwise to the mixture, and then 1 g of sodium cyanoborohydride is added. The mixture is stirred at room temperature for 3 h. The reaction solution is diluted with dichloromethane and filtered through Celite.

The organic phase is washed with water and saturated sodium chloride solution, dried over sodium sulfate and concentrated in vacuo. The crude product is chromatographed on silica gel with ethyl acetate/heptane (1/2). 0.72 g of the desired product is obtained. $C_{14}H_{14}O_2$ (214.27) MS (ESI$^+$):232.20 (M+NH$_4^+$)$^+$

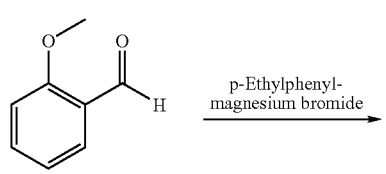

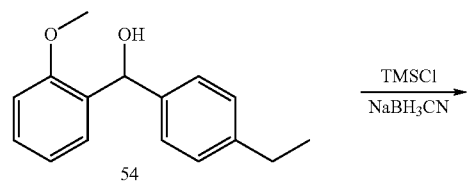

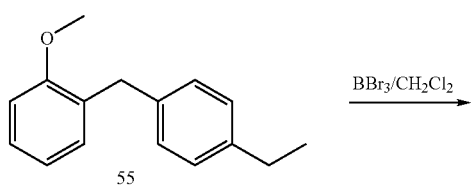

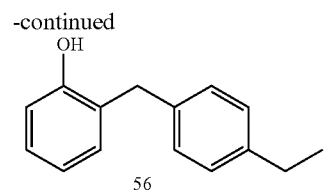

56

(4-Ethylphenyl)(2-methoxyphenyl)methanol 54

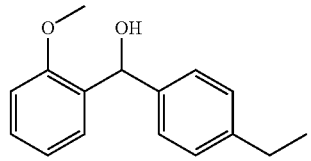

54

1.01 g of o-anisaldehyde are dissolved in THF and cooled to 0° C. 16.29 ml of 4-ethylphenylmagnesium bromide (0.5 M in THF) are added to the mixture. The reaction solution is stirred at room temperature overnight and then poured into 20% NH$_4$Cl solution and extracted with ethyl acetate. 1.92 g of the product are obtained, and this can be employed without further purification. $C_{16}H_{18}O_2$ (242.32) MS (ESI$^+$) 225.15 (M−OH)$^+$ (4-Ethylphenyl)(2-methoxyphenyl)methane 55

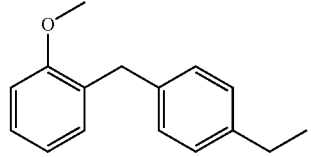

55

1.34 g of (4-ethylphenyl)(2-methoxyphenyl)methanol are dissolved in acetonitrile and cooled to 0° C. 1.50 g of sodium cyanoborohydride are added to the mixture and then 3.00 ml of trimethylsilyl chloride are added. The mixture is stirred at room temperature overnight. The reaction solution is filtered through Celite and extracted with saturated NaCl solution. The organic phase is dried over sodium sulfate and concentrated. The crude product is chromatographed on silica gel with ethyl acetate/heptane (1/12). 0.83 g of the product is obtained. $C_{16}H_{18}O$ (226.32) MS (DCI) 227.4 (M+H$^+$)

2-(4-Ethylbenzyl)phenol 56

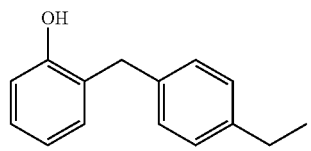

56

0.83 g of (4-ethylphenyl)(2-methoxyphenyl)methane 55 is dissolved in dichloromethane. 11.0 ml of boron tribromide (1 M in $CH_2Cl_2$) are added dropwise to the mixture. The mixture is stirred at room temperature for 5 hours and, after addition of water, the dichloromethane phase is separated off. The aqueous phase is extracted with ethyl acetate. The combined organic phases are washed with water and NaCl solution, dried over sodium sulfate and concentrated. 0.77 g is obtained as crude product which can be purified by chromatography. $C_{15}H_{16}O$ (212.29) MS (ESI): 235.20 (M+Na$^+$)

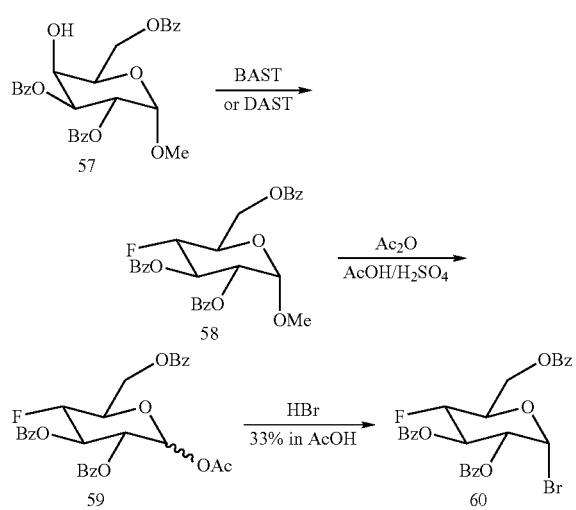

Methyl 2,3,6-tri-O-benzoyl-4-fluoro-4-deoxy-α-D-glucopyranoside 58

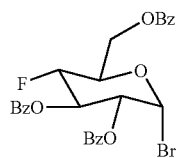

58

3 g of methyl 2,3,6-tri-O-benzoyl-α-D-galactopyranoside 57 (Reist et al., J. Org. Chem 1965, 30, 2312) are introduced into dichloromethane and cooled to −30° C. Then 3.06 ml of [bis(2-methoxyethyl)amino]sulfur trifluoride (BAST) are added dropwise. The reaction solution is warmed to room temperature and stirred overnight. The mixture is diluted with dichloromethane, and the organic phase is extracted with H$_2$O, NaHCO$_3$ solution and saturated NaCl solution. The organic phase is dried over Na$_2$SO$_4$ and concentrated. The crude product is crystallized from ethyl acetate and heptane. 1.95 g of 58 are obtained as a colorless solid. $C_{28}H_{25}FO_8$ (508.51) MS (ESI$^+$) 526.18 (M+NH$_4^+$). Alternatively, the reaction can also be carried out using 2.8 eq. of diethylaminosulfur trifluoride (DAST); in this case, the reaction solution is refluxed for 18 h after the addition. The working up takes place in analogy to the above description.

1-O-Acetyl-2,3,6-tri-O-benzoyl-4-fluoro-4-deoxy-glucose 59

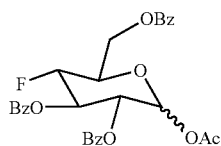

12 g of methyl 2,3,6-tri-O-benzoyl-4-fluoro-4-deoxy-α-D-glucopyranoside 58 are suspended in 150 ml of acetic anhydride. 8.4 ml of conc. sulfuric acid are mixed with 150 ml of glacial acetic acid and added to the mixture while cooling in ice. The mixture stirs at room temperature for 60 h. The mixture is poured into NaHCO$_3$ solution, and this solution is extracted with dichloromethane. The organic phase is extracted with NaCl solution, dried with Na$_2$SO$_4$ and concentrated. The residue is recrystallized from ethyl acetate/heptane. 5.97 g of the product are obtained as a colorless solid. $C_{29}H_{25}FO_9$(536.52) MS (ESI$^+$) 554.15 (M+NH$_4^+$)

2,3,6-Tri-O-benzoyl-4-fluoro-4-deoxyglucosyl bromide 60

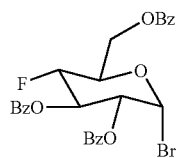

1.44 g of 1-O-acetyl-2,3,6-tri-O-benzoyl-4-fluoro-4-deoxyglucose are dissolved in 20 ml of hydrobromic acid in glacial acetic acid (33%) and stirred at room temperature. After 5 hours, the mixture is poured into ice-water, and the aqueous phase is extracted three times with dichloromethane. The collected organic phase is extracted with saturated sodium chloride solution, dried over sodium sulfate and evaporated to dryness. The crude product is filtered through a silica gel column with ethyl acetate/heptane 70:30.1.40 g of the product are obtained as a solid. $C_{27}H_{22}BrFO_7$ (557.37) MS (ESI$^+$) 574.05/576.05 (M+NH$_4^+$)

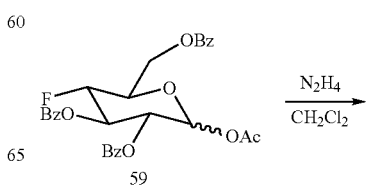

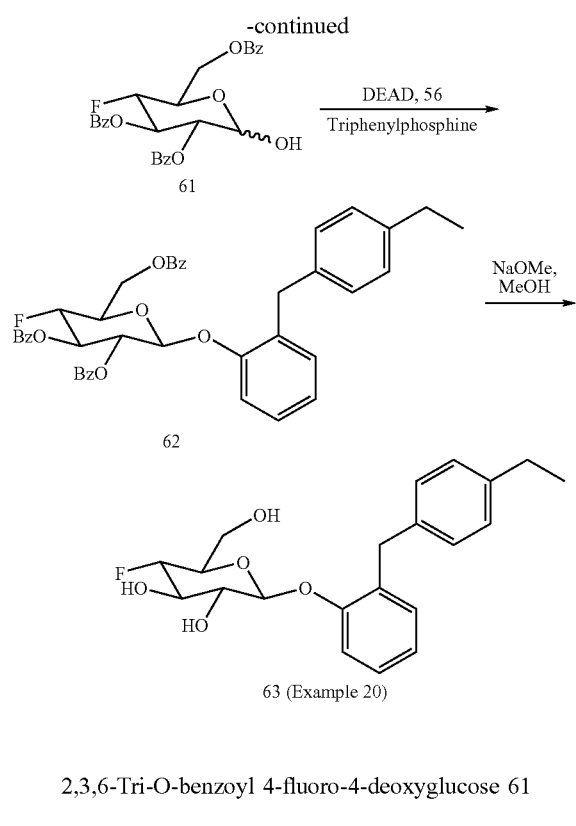

2,3,6-Tri-O-benzoyl 4-fluoro-4-deoxyglucose 61

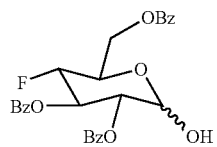

61

1.60 g of 1-O-acetyl-2,3,6-tri-O-benzoyl-4-fluoro-4-deoxyglucose are dissolved in dichloromethane. 173 µl of hydrazine hydrate are added to this solution. After 16 h, the reaction solution is partitioned between dichloromethane and H$_2$O. The organic phase is extracted with NaCl solution, dried over sodium sulfate and evaporated to dryness. The crude product is purified by column filtration. 1.22 g of the desired product are obtained. C$_{27}$H$_{23}$FO$_8$ (494.48) MS (ESI$^+$): 512.15 (M+NH$_4$$^+$).

Compound 62

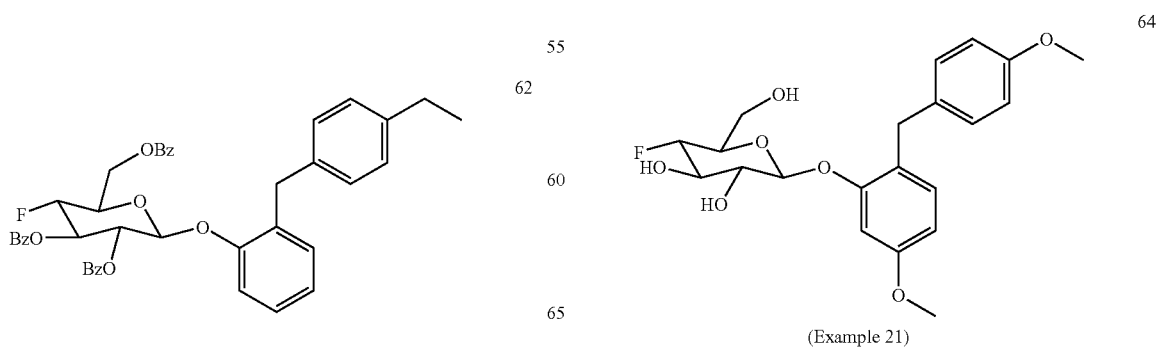

248 mg of 2-(4-ethylbenzyl)phenol (56), 550 mg of 2,3,6-tri-O-benzoyl-4-fluoro-4-deoxyglucose (61) and 335 mg of triphenylphosphine in 2 ml of dry dichloromethane are cooled to 0° C. under argon. 0.193 ml of diethyl azodicarboxylate is slowly added dropwise. This solution is brought to room temperature and stirs overnight. The solution is then diluted with dichloromethane and extracted with water, 0.5 M NaOH and saturated NaCl solution. The organic phase is dried over sodium sulfate and concentrated in vacuo. The residue is purified by chromatography (heptane:ethyl acetate 3:1). 200 mg of the desired product are obtained. C$_{42}$H$_{37}$FO$_8$ (688.76) MS (ESI): 706.30 (M+NH$_4$)$^+$.

Example 20

Compound 63

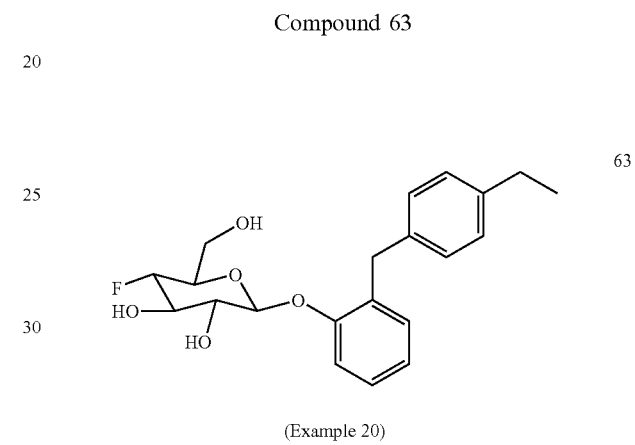

(Example 20)

200 mg of 62 are taken up in 10 ml of absolute methanol, and 1 ml of sodium methanolate solution (10 mg of sodium methanolate per ml of methanol) is added. The solution stirs for 8 h. Sodium is removed by adding Amberlyst 15 (H$^+$ form), the ion exchanger is filtered off, and the residue is thoroughly washed. The resulting product is purified by silica gel filtration (dichloromethane:methanol 96:4). 56 mg of the desired product are obtained. C$_{21}$H$_{25}$FO$_5$ (376.43) MS (ESI): 394.25 (M+NH$_4$$^+$)

The following examples are prepared in an analogous manner to example 20 using the appropriate aglycones:

(Example 21)

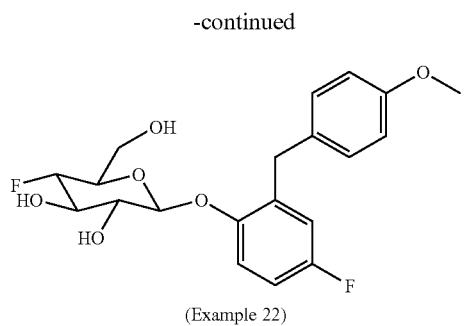

(Example 22)

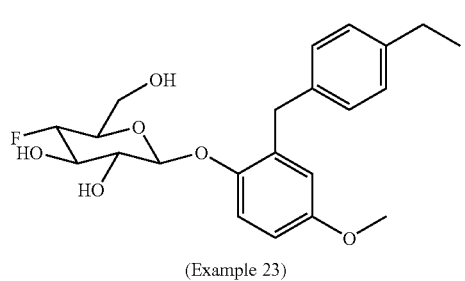

(Example 23)

The appropriate aglycones can be obtained for example by the processes described for compounds 7 or 56.

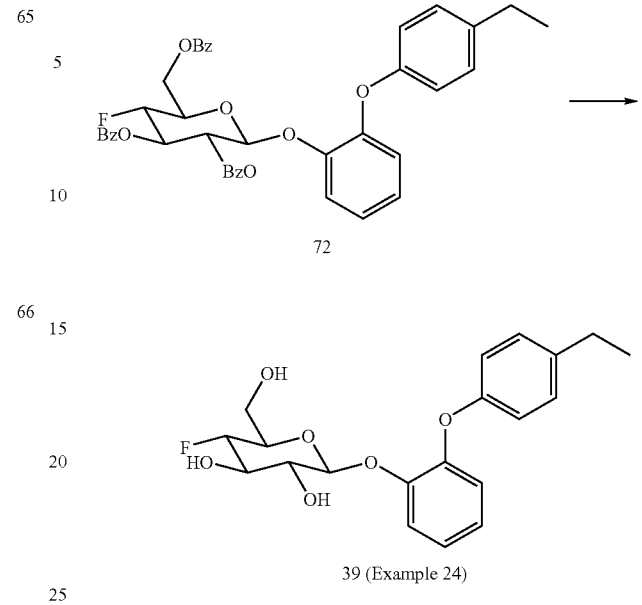

39 (Example 24)

1-[4-(2-Methoxyphenoxy)phenyl]ethanone 69

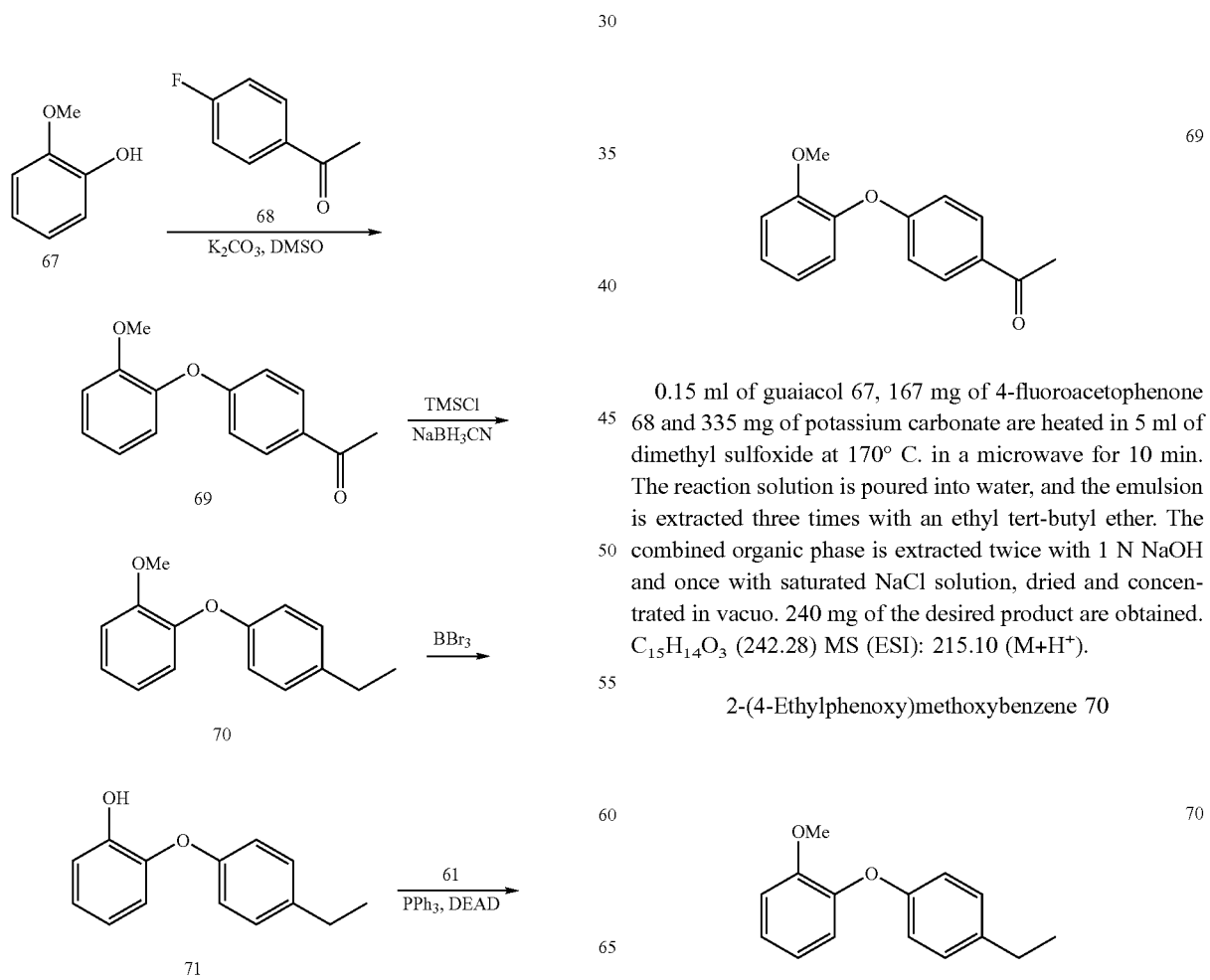

0.15 ml of guaiacol 67, 167 mg of 4-fluoroacetophenone 68 and 335 mg of potassium carbonate are heated in 5 ml of dimethyl sulfoxide at 170° C. in a microwave for 10 min. The reaction solution is poured into water, and the emulsion is extracted three times with an ethyl tert-butyl ether. The combined organic phase is extracted twice with 1 N NaOH and once with saturated NaCl solution, dried and concentrated in vacuo. 240 mg of the desired product are obtained. $C_{15}H_{14}O_3$ (242.28) MS (ESI): 215.10 (M+H$^+$).

2-(4-Ethylphenoxy)methoxybenzene 70

960 mg of 1-[4-(2-methoxyphenoxy)phenyl]ethanone 69 are dissolved in 20 ml of acetonitrile and cooled in an ice bath, and 1.05 g of sodium cyanoborohydride and 2.01 ml of trimethylsilyl chloride are added. After 1 h, the mixture is diluted with dichloromethane and filtered through Celite, and the organic phase is extracted with sodium chloride solution, dried over sodium sulfate and concentrated. The residue is purified by chromatography (heptane:ethyl acetate 7:1). 710 mg of the desired product are obtained. $C_{15}H_{16}O_2$ (228.29) MS (ESI): 246.20 (M+NH$_4^+$).

2-(4-Ethylphenoxy)phenol 71

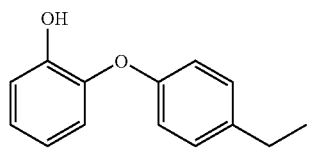

710 mg of 2-(4-ethylphenoxy)methoxybenzene 70 are dissolved in 5 ml absolute dichloromethane. 0.6 ml of boron tribromide (1 M dichloromethane) is added dropwise, and the solution stirs for 6 h. Further BBr$_3$ is added and the mixture is stirred until the reaction is almost complete according to LCMS. The solution is brought into ice-water, the organic phase is separated off, and the aqueous phase is extracted three times with dichloromethane. The combined organic phase is dried, evaporated to dryness and purified by chromatography. 450 mg of the desired product are obtained. $C_{14}H_{14}O_2$ (214.27) MS (ESI): 215.10 (M+H$^+$).

Compound 72

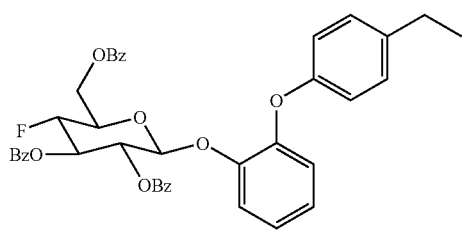

Compound 61 (466 mg) and phenol 71 (242 mg) are reacted in analogy to the synthesis of compound 62. The resulting product can be purified by column chromatography (heptane:ethyl acetate 4:1). 240 mg of the desired product are obtained. $C_{41}H_{35}FO_9$(690.73) MS (ESI): 708.25 (M+NH$_4^+$).

Example 24

Compound 39

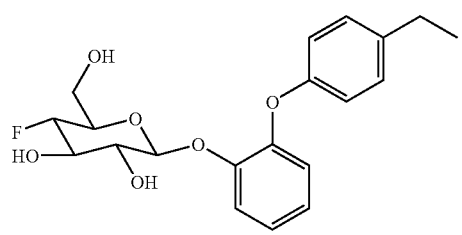

(Example 24)

230 mg of compound 72 are reacted with sodium methanolate in analogy to the liberation of example 20. The compound can be purified by silica gel chromatography (dichloromethane:methanol 96:4). 119 mg of the desired product are obtained. $C_{20}H_{23}FO_6$(378.40) MS (ESI): 396.15 (M+NH$_4^+$).

We claim:
1. A compound of formula I

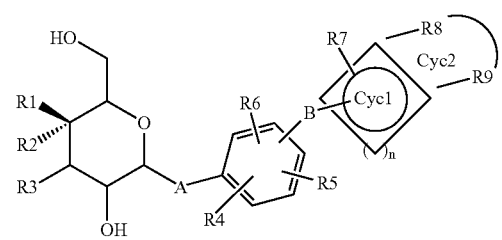

wherein:
R1, R2 are each independently OH, F or H with the proviso that
when R1 is F, R2 cannot be OH;
when R1 is OH, R2 cannot be F; and
when R1 is OH, R2 cannot be OH;
R3 is OH or F,
with the proviso that at least one of said R1, R2, R3 radicals must be F;
A is O, NH, CH$_2$, S or a bond;
R4, R5, R6 are each independently hydrogen, F, Cl, Br, I, OH, NO$_2$, CN, COOH,
CO(C$_1$-C$_6$)-alkyl, COO(C$_1$-C$_6$)-alkyl, CONH$_2$, CONH (C$_1$-C$_6$)-alkyl, CON[(C$_1$-C$_6$)-alkyl]$_2$, (C$_1$-C$_6$)-alkyl, (C$_2$-C$_6$)-alkenyl, (C$_2$-C$_6$)-alkynyl, (C$_1$-C$_6$)-alkoxy, HO(C$_1$-C$_6$)-alkyl, (C$_1$-C$_6$)-alkyl-O—(C$_1$-C$_6$)-alkyl, phenyl or benzyl,
wherein said CO(C$_1$-C$_6$)-alkyl, COO(C$_1$-C$_6$)-alkyl, CONH(C$_1$-C$_6$)-alkyl, CON[(C$_1$-C$_6$)-alkyl]$_2$, (C$_1$-C$_6$)-alkyl, (C$_2$-C$_6$)-alkenyl, (C$_2$-C$_6$)-alkynyl, (C$_1$-C$_6$)-alkoxy, HO(C$_1$-C$_6$)-alkyl, (C$_1$-C$_6$)-alkyl-O—(C$_1$-C$_6$)-alkyl radicals are optionally substituted with one or more fluorine atoms,
SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_o$-phenyl, SO—

($C_1$-$C_6$)-alkyl, SO—($CH_2$)$_o$-phenyl, $SO_2$—($C_1$-$C_6$)-alkyl, $SO_2$—($CH_2$)$_o$-phenyl,
  wherein the phenyl ring of said S—($CH_2$)$_o$-phenyl, SO—($CH_2$)$_o$-phenyl and $SO_2$—($CH_2$)$_o$-phenyl radicals may be mono- or disubstituted with F, Cl, Br, OH, $CF_3$, $NO_2$, CN, $OCF_3$, O—($C_1$-$C_6$)-alkyl, ($C_1$-$C_6$)-alkyl or $NH_2$ and wherein o is 0, 1, 2, 3, 4, 5 or 6,
$NH_2$, NH—($C_1$-$C_6$)-alkyl, N(($C_1$-$C_6$)-alkyl)$_2$, NH($C_1$-$C_7$)-acyl, phenyl, O—($CH_2$)$_o$-phenyl,
  wherein the phenyl ring of said phenyl and O—($CH_2$)$_o$-phenyl radicals may be mono-, di-, or trisubstituted with F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl or $CONH_2$ and wherein o is as hereinabove defined;

B is ($C_0$-$C_{15}$)-alkanediyl,
  wherein one or more carbon atoms in said ($C_0$-$C_{15}$)-alkanediyl radical are, independently of one another, optionally replaced by —O—, —(C=O)—, —CH=CH—, —C≡C—, —S—, —CH(OH)—, —CHF—, —$CF_2$—, —(S=O)—, —($SO_2$)—, —N(($C_1$-$C_6$)-alkyl)-, —N(($C_1$-$C_6$)-alkyl-phenyl)- or —NH—;

n is 0, 1, 2, 3 or 4;

Cyc1 is a 3-, 4-, 5-, 6-, or 7-membered saturated, partially saturated or unsaturated ring, wherein one carbon atom of said ring may be replaced by O, N or S;

R7, R8, R9 R7, R8, and R9 are each independently hydrogen, F, Cl, Br, I, OH, CF3, $NO_2$,
  CN, COOH, COO($C_1$-$C_6$)-alkyl, CO($C_1$-$C_4$)-alkyl, $CONH_2$, CONH($C_1$-$C_6$)-alkyl, CON[($C_1$-$C_6$)-alkyl]$_2$, ($C_1$-$C_6$)-alkyl, ($C_2$-$C_6$)-alkenyl, ($C_2$-$C_6$)-alkynyl, ($C_1$-$C_8$)-alkoxy, HO—($C_1$-$C_6$)-alkyl and ($C_1$-$C_6$)-alkyl-O—($C_1$-$C_6$)-alkyl,
    wherein said COO($C_1$-$C_6$)-alkyl, CO($C_1$-$C_4$)-alkyl, CONH($C_1$-$C_6$)-alkyl, CON[($C_1$-$C_6$)-alkyl]$_2$, ($C_1$-$C_6$)-alkyl, ($C_2$-$C_6$)-alkenyl, ($C_2$-$C_6$)-alkynyl, ($C_1$-$C_8$)-alkoxy, HO—($C_1$-$C_6$)-alkyl and ($C_1$-$C_6$)-alkyl-O—($C_1$-$C_6$)-alkyl radicals are optionally substituted with one or more fluorine atoms,
  $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_o$-phenyl, SO—($C_1$-$C_6$)-alkyl, SO—($CH_2$)$_o$-phenyl, $SO_2$—($C_1$-$C_6$)-alkyl, $SO_2$—($CH_2$)$_o$-phenyl,
    wherein said $SO_2NH$($C_1$-$C_6$)-alkyl, $SO_2N$[($C_1$-$C_6$)-alkyl]$_2$, S—($C_1$-$C_6$)-alkyl, SO—($C_1$-$C_6$)-alkyl and $SO_2$—($C_1$-$C_6$)-alkyl radicals are optionally substituted with one or more fluorine atoms, and wherein the phenyl ring of said
    S—($CH_2$)$_o$-phenyl, SO—($CH_2$)$_o$-phenyl and $SO_2$—($CH_2$)$_o$-phenyl radicals is optionally mono- or disubstituted with F, Cl, Br, OH, $CF_3$, $NO_2$, CN, $OCF_3$, O—($C_1$-$C_6$)-alkyl, ($C_1$-$C_6$)-alkyl or $NH_2$ and wherein o is as hereinabove defined,
  $NH_2$, NH—($C_1$-$C_6$)-alkyl, N(($C_1$-$C_6$)-alkyl)$_2$, NH($C_1$-$C_7$)-acyl, phenyl or O—($CH_2$)$_o$-phenyl,
    wherein the phenyl ring of said phenyl and O—($CH_2$)$_o$-phenyl radicals is optionally mono-, di-, or trisubstituted with F, Cl, Br, I, OH, CF3, $NO_2$, CN, $OCF_3$, ($C_1$-$C_8$)-alkoxy, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl or $CONH_2$, and wherein o is as hereinabove defined;
  or R8 and R9 taken together with the carbon atoms to which they are attached form a 5-, 6- or 7-membered, saturated, partially saturated or unsaturated ring herein referred to as Cyc2,
    wherein one or two carbon atom(s) in said Cyc2 ring are optionally replaced by N, O or S, and wherein said Cyc2 ring is optionally substituted with ($C_1$-$C_6$)-alkyl, ($C_2$-$C_5$)-alkenyl or ($C_2$-$C_5$)-alkynyl,
      wherein said ($C_1$-$C_6$)-alkyl, ($C_2$-$C_5$)-alkenyl and ($C_2$-$C_5$)-alkynyl radicals are optionally substituted with F, Cl, OH, $CF_3$, $NO_2$, CN, COO($C_1$-$C_4$)-alkyl, $CONH_2$, CONH($C_1$-$C_4$)-alkyl or $OCF_3$, and wherein a —$CH_2$— group contained in said ($C_1$-$C_6$)-alkyl, ($C_2$-$C_5$)-alkenyl and ($C_2$-$C_5$)-alkynyl radicals is optionally replaced by —O—;

and pharmaceutically acceptable salts thereof.

2. The compound of claim 1 wherein:
R1 and R2 are each independently OH, F or H,
  with the proviso that at least one of said radicals R1 and R2 must be F and with the further proviso that
  when R1 is F, R2 is not OH,
  when R1 is OH, R2 is not F, and
  when R1 is OH, R2 is not OH;
R3 is OH;
A is O or NH;
R4, R5, R6 are each independently hydrogen, F, Cl, Br, I, OH, $NO_2$, CN, COOH,
  CO($C_1$-$C_6$)-alkyl, COO($C_1$-$C_6$)-alkyl, $CONH_2$, CONH($C_1$-$C_6$)-alkyl, CON[($C_1$-$C_6$)-alkyl]$_2$, ($C_1$-$C_6$)-alkyl, ($C_2$-$C_6$)-alkenyl, ($C_2$-$C_6$)-alkynyl, ($C_1$-$C_6$)-alkoxy, HO($C_1$-$C_6$)-alkyl, ($C_1$-$C_6$)-alkyl-O—($C_1$-$C_6$)-alkyl, phenyl, benzyl or SO—($C_1$-$C_6$)-alkyl,
    wherein said CO($C_1$-$C_6$)-alkyl, COO($C_1$-$C_6$)-alkyl, CONH($C_1$-$C_6$)-alkyl, CON[($C_1$-$C_6$)-alkyl)]$_2$, ($C_1$-$C_6$)-alkyl, ($C_2$-$C_6$)-alkenyl, ($C_2$-$C_6$)-alkynyl, ($C_1$-$C_6$)-alkoxy, HO($C_1$-$C_6$)-alkyl, ($C_1$-$C_6$)-alkyl-O—($C_1$-$C_6$)-alkyl and SO—($C_1$-$C_6$)-alkyl radicals are optionally substituted with one or more fluorine atoms, B is ($C_0$-$C_{15}$)-alkanediyl, wherein one or more of the carbon atoms in said alkanediyl radical may be replaced, independently of one another, with —O—, —(C=O)—, —CH=CH—, —C≡C—, —S—, —CH(OH)—, —CHF—, —$CF_2$—, —(S=O)—, —($SO_2$)—, —N(($C_1$-$C_6$)-alkyl)-, —N(($C_1$-$C_6$)-alkyl-phenyl)- or —NH—;

n is 0, 1, 2, 3 or 4;

Cyc1 is a 3-, 4-, 5-, 6- or 7-membered saturated, partially saturated or unsaturated ring, wherein one carbon atom of said ring may be replaced by O, N or S;

R7, R8, and R9 are each independently hydrogen, F, Cl, Br, I, OH, $CF_3$, $NO_2$, CN, COOH,
  COO($C_1$-$C_6$)-alkyl, CO($C_1$-$C_4$)-alkyl, $CONH_2$, CONH($C_1$-$C_6$)-alkyl, CON[($C_1$-$C_6$)-alkyl]$_2$, ($C_1$-$C_6$)-alkyl, ($C_2$-$C_6$)-alkenyl, ($C_2$-$C_6$)-alkynyl, ($C_1$-$C_8$)-alkoxy, HO—($C_1$-$C_6$)-alkyl, ($C_1$-$C_6$)-alkyl-O—($C_1$-$C_6$)-alkyl or SO—($C_1$-$C_6$)-alkyl,
    wherein said COO($C_1$-$C_6$)-alkyl, CO($C_1$-$C_4$)-alkyl, CONH($C_1$-$C_6$)-alkyl, CON[($C_1$-$C_6$)-alkyl]$_2$, ($C_1$-$C_6$)-alkyl, ($C_2$-$C_6$)-alkenyl, ($C_2$-$C_6$)-alkynyl, ($C_1$-$C_8$)-alkoxy, HO—($C_1$-$C_6$)-alkyl, ($C_1$-$C_6$)-alkyl-O—($C_1$-$C_6$)-alkyl and SO—($C_1$-$C_6$)-alkyl radicals are optionally substituted with one or more fluorine atoms,
  or R8 and R9 taken together with the carbon atoms to which they are attached form a 5-, 6- or 7-membered, saturated, partially saturated or unsaturated ring herein referred to as Cyc2, wherein one or two carbon atom(s) in said Cyc2 ring are optionally replaced by N, O or S, and wherein said Cyc2 ring is optionally substituted with $(C_1-C_6)$-alkyl, $(C_2-C_5)$-alkenyl or $(C_2-C_5)$-alkynyl, wherein said $(C_1-C_6)$-alkyl, $(C_2-C_5)$-alkenyl and $(C_2-C_5)$-alkynyl radicals are optionally substituted with F, Cl, OH, $CF_3$, $NO_2$, CN, $COO(C_1-C_4)$-alkyl, $CONH_2$, $CONH(C_1-C_4)$-alkyl or $OCF_3$, and wherein a —CH2-group contained in said $(C_1-C_6)$-alkyl, $(C_2-C_5)$-alkenyl and $(C_2-C_5)$-alkynyl radicals is optionally replaced by —O—.

3. The compound of claim 1 wherein the sugar residues are beta(β)-linked and the stereochemistry in the 2, 3 and 5 position of the sugar residue has the D-gluco configuration.

4. The compound of claim 1 wherein:
R1 and R2 are each independently OH, F or H, with the proviso that at least one of said radicals R1 and R2 must be F and with the further proviso that
when R1 is F, R2 is not OH,
when R1 is OH, R2 is not F, and
when R1 is OH, R2 is not OH,
R3 is OH;
A is O;
R4, R5, R6 are each independently hydrogen, F, Cl, Br, I, OH, $NO_2$, CN, COOH, CF3, OCF3, OCH2CF3, (C1-C4)alkyl-CF2—, $COO(C_1-C_6)$-alkyl, $(C_1-C_6)$-alkyl, $(C_2-C_6)$-alkenyl, $(C_2-C_6)$-alkynyl, $(C_1-C_6)$-alkoxy, $HO(C_1-C_6)$-alkyl, $(C_1-C_6)$-alkyl-O—$(C_1-C_6)$-alkyl, phenyl or benzyl,
B is (C1-C4)-alkanediyl, wherein one or more of the carbon atoms in said alkanediyl radical may be replaced, independently of one another, with —O—, —(C=O)—, —CH(OH)—, —CHF—, —CF$_2$—, —CO—N($C_1-C_6$)-alkyl)-, —CO—NH— or —NH—;
n is 2 or 3;
Cyc1 is an unsaturated 5- or 6-membered ring, wherein one carbon atom of said ring may be replaced by O, N or S;
R7, R8, and R9 are each independently hydrogen, F, Cl, Br, OH, $(C_1-C_6)$-alkyl, $(C_1-C_8)$-alkoxy, HO—$(C_1-C_6)$-alkyl or $(C_1-C_6)$-alkyl-O—$(C_1-C_6)$-alkyl,
or R8 and R9 taken together form the radicals —CH=CH—O—, —CH2—CH2-O—, —CH=CH—S—, —CH=CH—CH=CH—, —O—$(CH_2)_p$—O— wherein p is 1 or 2 and with the carbon atoms to which said radicals are attached form a 5- or 6-membered, saturated, partially saturated or completely unsaturated ring and, in such instance, R7 is preferably methyl, ethyl, OMe, F, Cl, Br or H.

5. The compound of claim 1 wherein:
R1 is F and R2 is H;
R1 is H and R2 is F; or
R1 is F and R2 is F
R3 is OH;
A is O;
R4, R5, R6 are each independently hydrogen, OH, $(C_1-C_4)$-alkoxy, $CF_3$, $(C_1-C_4)$-alkyl, F, Cl, Br or I
B is —$CH_2$—, —$C_2H_4$—, —$C_3H_6$—, —CH(OH)—, —(C=O)—, —CO—NH—$CH_2$—, —CO—$CH_2$—$CH_2$—, —O— or —NH—;
n is 2 or 3;
Cyc1 is an unsaturated 6-membered ring, wherein one carbon atom of said 6-membered ring may be replaced by N, or an unsaturated 5-membered ring, wherein one carbon atom of said 5-membered ring may be replaced by S;
R7, R8, R9 are each independently hydrogen, OH, $(C_1-C_4)$-alkyl, $(C_1-C_7)$-alkoxy, $OCF_3$ or halogen or
R8 and R9 taken together form the radicals —CH=CH—O—, —$CH_2$—$CH_2$—O—, —CH=CH—CH=CH— or —O—$(CH_2)_p$—O— wherein p is 1 or 2, and, with the carbon atoms to which they are attached, form a 5- or 6-membered ring, and, in such instance, R7 is preferably methyl, ethyl, methoxy, F, Cl, Br or hydrogen.

6. A compound of the formula Ia

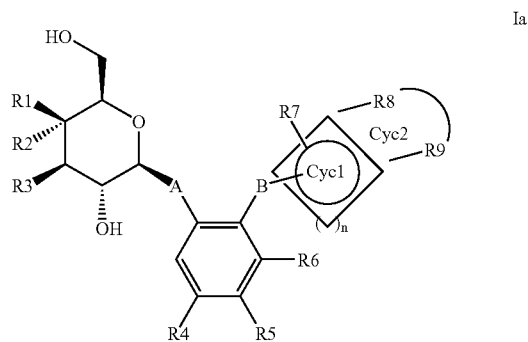

wherein
R1 is F and R2 is H;
R1 is H and R2 is F; or
R1 is F and R2 is F;
R3 is OH;
A is O;
R4 is hydrogen, $(C_1-C_4)$-alkyl, $(C_1-C_4)$-alkoxy or OH;
R5 is hydrogen, F. methoxy or ethoxy;
R6 is hydrogen or OH;
B is —$CH_2$—, —CO—NH—$CH_2$—; —O-or —CO—$CH_2$—$CH_2$—;
Cyc1 is phenyl or thiophene;
R7, R8, R9 are hydrogen, OH, Cl, $OCF_3$, $(C_1-C_4)$-alkyl or $(C_1-C_4)$-alkoxy; or
R8 and R9 taken together form —CH=CH—O—, —CH=CH—CH=CH— or —$CH_2$—$CH_2$—O— and, with the carbon atoms to which they are attached, form a 5- or 6-membered ring, and, in such instance, R7 is preferably hydrogen.

7. A compound of the formula Ib

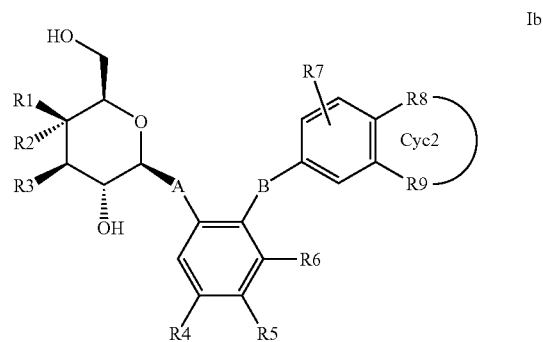

wherein
R1 is F and R2 is H;
R1 is H and R2 is F; or
R1 is F and R2 is F;
R3 is OH;
A is O;
R4 is hydrogen, methyl, methoxy or OH;
R5 is hydrogen, F or methoxy;
R6 is hydrogen or OH;
B is —$CH_2$—, —CO—NH—$CH_2$—, —O— or —CO—$CH_2$—$CH_2$—;
Cyc1 is phenyl;
R7 is hydrogen;
R8 is hydrogen, OH, ethyl, Cl, $OCF_3$ or methoxy;
R9 is hydrogen; or
R8 and R9 taken together form —CH=CH—O— or —$CH_2$—$CH_2$—O—, and, with the carbon atoms to which they are attached form a 5-membered ring.

8. A pharmaceutical composition comprising a compound of claim 1 and a pharmaceutically acceptable carrier.

9. A pharmaceutical composition comprising a compound of claim 1 and one or more blood glucose-lowering active ingredients.

10. A method of treating type 1 or type 2 diabetes which comprises administering to a patient in need thereof a therapeutically effective amount of a compound of claim 1.

11. A method of lowering blood glucose which comprises administering to a patient in need thereof a therapeutically effective amount of a compound of claim 1.

12. A method of treating type 1 or type 2 diabetes which comprises administering to a patient in need thereof a therapeutically effective amount of a compound of claim 1 with at least one other blood glucose-lowering active ingredient.

13. A method of lowering blood glucose which comprises administering to a patient in need thereof a therapeutically effective amount of a compound of claim 1 with at least one other blood glucose-lowering active ingredient.

* * * * *